(12) United States Patent
Adam et al.

(10) Patent No.: US 9,788,813 B2
(45) Date of Patent: Oct. 17, 2017

(54) MULTIPLE APERTURE PROBE INTERNAL APPARATUS AND CABLE ASSEMBLIES

(75) Inventors: Sharon L. Adam, San Jose, CA (US); David M. Smith, Lodi, CA (US); Donald F. Specht, Los Altos, CA (US); Kenneth D. Brewer, Santa Clara, CA (US)

(73) Assignee: MAUI IMAGING, INC., Sunnyvale, CA (US)

( * ) Notice: Subject to any disclaimer, the term of this patent is extended or adjusted under 35 U.S.C. 154(b) by 991 days.

(21) Appl. No.: 13/272,098

(22) Filed: Oct. 12, 2011

(65) Prior Publication Data

US 2012/0095347 A1    Apr. 19, 2012

Related U.S. Application Data

(60) Provisional application No. 61/392,841, filed on Oct. 13, 2010.

(51) Int. Cl.
*A61B 8/12*    (2006.01)
*A61B 8/00*    (2006.01)
(Continued)

(52) U.S. Cl.
CPC .............. *A61B 8/12* (2013.01); *A61B 8/4477* (2013.01); *A61B 8/4483* (2013.01);
(Continued)

(58) Field of Classification Search
USPC .................................................. 600/437, 459
See application file for complete search history.

(56) References Cited

U.S. PATENT DOCUMENTS

| | | |
|---|---|---|
| 3,174,286 A | 3/1965 | Erickson |
| 3,895,381 A | 7/1975 | Kock |
| | (Continued) | |

FOREIGN PATENT DOCUMENTS

| | | |
|---|---|---|
| CN | 1781460 | 6/2006 |
| CN | 101116622 A | 2/2008 |
| | (Continued) | |

OTHER PUBLICATIONS

Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filed and any foreign priority date) 1994.

(Continued)

*Primary Examiner* — Rochelle Turchen
(74) *Attorney, Agent, or Firm* — Shay Glenn LLP

(57) ABSTRACT

A Multiple Aperture Ultrasound Imaging (MAUI) probe or transducer is uniquely capable of simultaneous imaging of a region of interest from separate physical apertures of ultrasound arrays. The probe can include separate backing plates configured to secure the ultrasound arrays in predetermined positions and orientations relative to one another. Some embodiments of the probe include flex circuit connected to the ultrasound arrays. In additional embodiments, a flex/PC board comprising flex connectors and an array of terminals is connected to the ultrasound arrays. Algorithms can solve for variations in tissue speed of sound, thus allowing the probe apparatus to be used virtually anywhere in or on the body.

14 Claims, 17 Drawing Sheets

(51) Int. Cl.
  *G01S 15/89* (2006.01)
  *G10K 11/00* (2006.01)
  *G01S 7/52* (2006.01)

(52) U.S. Cl.
  CPC ...... *G01S 7/52079* (2013.01); *G01S 15/8915* (2013.01); *G01S 15/8927* (2013.01); *G10K 11/004* (2013.01); *G01S 7/52047* (2013.01)

(56) References Cited

U.S. PATENT DOCUMENTS

| | | |
|---|---|---|
| 3,974,692 A | 8/1976 | Hassler |
| 4,055,988 A | 11/1977 | Dutton |
| 4,072,922 A | 2/1978 | Taner et al. |
| 4,097,835 A | 6/1978 | Green |
| 4,105,018 A | 8/1978 | Greenleaf et al. |
| 4,180,792 A | 12/1979 | Lederman et al. |
| 4,259,733 A | 3/1981 | Taner et al. |
| 4,265,126 A | 5/1981 | Papadofrangakis et al. |
| 4,271,842 A | 6/1981 | Specht et al. |
| 4,325,257 A | 4/1982 | Kino et al. |
| 4,327,738 A | 5/1982 | Green et al. |
| 4,333,474 A | 6/1982 | Nigam |
| 4,339,952 A | 7/1982 | Foster |
| 4,452,084 A | 6/1984 | Taenzer |
| 4,501,279 A | 2/1985 | Seo |
| 4,511,998 A | 4/1985 | Kanda et al. |
| 4,539,847 A | 9/1985 | Paap |
| 4,566,459 A | 1/1986 | Umemura et al. |
| 4,567,768 A | 2/1986 | Satoh et al. |
| 4,604,697 A | 8/1986 | Luthra et al. |
| 4,662,222 A | 5/1987 | Johnson |
| 4,669,482 A | 6/1987 | Ophir |
| 4,682,497 A | 7/1987 | Sasaki |
| 4,781,199 A | 11/1988 | Hirama et al. |
| 4,817,434 A | 4/1989 | Anderson |
| 4,831,601 A | 5/1989 | Breimesser et al. |
| 4,893,284 A | 1/1990 | Magrane |
| 4,893,628 A | 1/1990 | Angelsen |
| 5,050,588 A | 9/1991 | Grey et al. |
| 5,141,738 A | 8/1992 | Rasor et al. |
| 5,161,536 A | 11/1992 | Vilkomerson et al. |
| 5,197,475 A | 3/1993 | Antich et al. |
| 5,226,019 A | 7/1993 | Bahorich |
| 5,230,339 A | 7/1993 | Charlebois |
| 5,269,309 A | 12/1993 | Fort et al. |
| 5,278,757 A | 1/1994 | Hoctor et al. |
| 5,293,871 A | 3/1994 | Reinstein et al. |
| 5,299,576 A | 4/1994 | Shiba |
| 5,301,674 A | 4/1994 | Erikson et al. |
| 5,305,756 A | 4/1994 | Entrekin et al. |
| 5,339,282 A | 8/1994 | Kuhn et al. |
| 5,345,426 A | 9/1994 | Lipschutz |
| 5,349,960 A | 9/1994 | Gondo |
| 5,355,888 A | 10/1994 | Kendall |
| 5,381,794 A | 1/1995 | Tei et al. |
| 5,398,216 A | 3/1995 | Hall et al. |
| 5,409,010 A | 4/1995 | Beach et al. |
| 5,442,462 A | 8/1995 | Guissin |
| 5,454,372 A | 10/1995 | Banjanin et al. |
| 5,503,152 A | 4/1996 | Oakley et al. |
| 5,515,853 A | 5/1996 | Smith et al. |
| 5,515,856 A | 5/1996 | Olstad et al. |
| 5,522,393 A | 6/1996 | Phillips et al. |
| 5,526,815 A | 6/1996 | Granz et al. |
| 5,544,659 A | 8/1996 | Banjanin |
| 5,558,092 A | 9/1996 | Unger et al. |
| 5,564,423 A | 10/1996 | Mele et al. |
| 5,568,812 A | 10/1996 | Murashita et al. |
| 5,570,691 A | 11/1996 | Wright et al. |
| 5,581,517 A | 12/1996 | Gee et al. |
| 5,628,320 A | 5/1997 | Teo |
| 5,673,697 A | 10/1997 | Bryan et al. |
| 5,675,550 A | 10/1997 | Ekhaus |
| 5,720,291 A | 2/1998 | Schwartz |
| 5,720,708 A | 2/1998 | Lu et al. |
| 5,744,898 A | 4/1998 | Smith et al. |
| 5,769,079 A | 6/1998 | Hossack |
| 5,784,334 A | 7/1998 | Sena et al. |
| 5,785,654 A | 7/1998 | Iinuma et al. |
| 5,795,297 A | 8/1998 | Daigle |
| 5,797,845 A | 8/1998 | Barabash et al. |
| 5,798,459 A | 8/1998 | Ohba et al. |
| 5,820,561 A | 10/1998 | Olstad et al. |
| 5,838,564 A | 11/1998 | Bahorich et al. |
| 5,850,622 A | 12/1998 | Vassiliou et al. |
| 5,862,100 A | 1/1999 | VerWest |
| 5,870,691 A | 2/1999 | Partyka et al. |
| 5,876,342 A | 3/1999 | Chen et al. |
| 5,891,038 A | 4/1999 | Seyed-Bolorforosh et al. |
| 5,892,732 A | 4/1999 | Gersztenkorn |
| 5,916,169 A | 6/1999 | Hanafy et al. |
| 5,919,139 A | 7/1999 | Lin |
| 5,920,285 A | 7/1999 | Benjamin |
| 5,930,730 A | 7/1999 | Marfurt et al. |
| 5,940,778 A | 8/1999 | Marfurt et al. |
| 5,951,479 A | 9/1999 | Holm et al. |
| 5,964,707 A | 10/1999 | Fenster et al. |
| 5,969,661 A | 10/1999 | Benjamin |
| 5,999,836 A | 12/1999 | Nelson et al. |
| 6,007,499 A | 12/1999 | Martin et al. |
| 6,013,032 A | 1/2000 | Savord |
| 6,014,473 A | 1/2000 | Hossack et al. |
| 6,048,315 A | 4/2000 | Chiao et al. |
| 6,049,509 A | 4/2000 | Sonneland et al. |
| 6,050,943 A | 4/2000 | Slayton et al. |
| 6,056,693 A | 5/2000 | Haider |
| 6,058,074 A | 5/2000 | Swan et al. |
| 6,077,224 A | 6/2000 | Lang et al. |
| 6,092,026 A | 7/2000 | Bahorich et al. |
| 6,122,538 A | 9/2000 | Sliwa, Jr. et al. |
| 6,123,670 A | 9/2000 | Mo |
| 6,129,672 A | 10/2000 | Seward et al. |
| 6,135,960 A | 10/2000 | Holmberg |
| 6,138,075 A | 10/2000 | Yost |
| 6,148,095 A | 11/2000 | Prause et al. |
| 6,162,175 A | 12/2000 | Marian, Jr. et al. |
| 6,166,384 A | 12/2000 | Dentinger et al. |
| 6,166,853 A | 12/2000 | Sapia et al. |
| 6,193,665 B1 | 2/2001 | Hall et al. |
| 6,196,739 B1 | 3/2001 | Silverbrook |
| 6,200,266 B1 | 3/2001 | Shokrollahi et al. |
| 6,210,335 B1 | 4/2001 | Miller |
| 6,213,958 B1 | 4/2001 | Winder |
| 6,221,019 B1 | 4/2001 | Kantorovich |
| 6,231,511 B1 | 5/2001 | Bae |
| 6,238,342 B1 | 5/2001 | Feleppa et al. |
| 6,246,901 B1 | 6/2001 | Benaron |
| 6,251,073 B1 | 6/2001 | Imran et al. |
| 6,264,609 B1 | 7/2001 | Herrington et al. |
| 6,266,551 B1 | 7/2001 | Osadchy et al. |
| 6,278,949 B1 | 8/2001 | Alam |
| 6,289,230 B1 | 9/2001 | Chaiken et al. |
| 6,299,580 B1 | 10/2001 | Asafusa |
| 6,304,684 B1 | 10/2001 | Niczyporuk et al. |
| 6,309,356 B1 | 10/2001 | Ustuner et al. |
| 6,324,453 B1 | 11/2001 | Breed et al. |
| 6,345,539 B1 | 2/2002 | Rawes et al. |
| 6,361,500 B1 | 3/2002 | Masters |
| 6,363,033 B1 | 3/2002 | Cole et al. |
| 6,370,480 B1 | 4/2002 | Gupta et al. |
| 6,374,185 B1 | 4/2002 | Taner et al. |
| 6,394,955 B1 | 5/2002 | Perlitz |
| 6,423,002 B1 | 7/2002 | Hossack |
| 6,436,046 B1 | 8/2002 | Napolitano et al. |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,475,150 B2 | 11/2002 | Haddad |
| 6,480,790 B1 | 11/2002 | Calvert et al. |
| 6,487,502 B1 | 11/2002 | Taner |
| 6,499,536 B1 | 12/2002 | Ellingsen |
| 6,508,768 B1 | 1/2003 | Hall et al. |

(56) References Cited

U.S. PATENT DOCUMENTS

| | | |
|---|---|---|
| 6,508,770 B1 | 1/2003 | Cai |
| 6,517,484 B1 | 2/2003 | Wilk et al. |
| 6,526,163 B1 | 2/2003 | Halmann et al. |
| 6,543,272 B1 | 4/2003 | Vitek |
| 6,547,732 B2 | 4/2003 | Jago |
| 6,551,246 B1 | 4/2003 | Ustuner et al. |
| 6,565,510 B1 | 5/2003 | Haider |
| 6,585,647 B1 | 7/2003 | Winder |
| 6,604,421 B1 | 8/2003 | Li |
| 6,614,560 B1 | 9/2003 | Silverbrook |
| 6,620,101 B2 | 9/2003 | Azzam et al. |
| 6,652,461 B1 | 11/2003 | Levkovitz |
| 6,668,654 B2 | 12/2003 | Dubois et al. |
| 6,672,165 B2 | 1/2004 | Rather et al. |
| 6,681,185 B1 | 1/2004 | Young et al. |
| 6,690,816 B2 | 2/2004 | Aylward et al. |
| 6,692,450 B1 | 2/2004 | Coleman |
| 6,695,778 B2 | 2/2004 | Golland et al. |
| 6,702,745 B1 | 3/2004 | Smythe |
| 6,719,693 B2 | 4/2004 | Richard |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,837,853 B2 | 1/2005 | Marian |
| 6,843,770 B2 | 1/2005 | Sumanaweera |
| 6,847,737 B1 | 1/2005 | Kouri et al. |
| 6,854,332 B2 | 2/2005 | Alleyne |
| 6,865,140 B2 | 3/2005 | Thomenius et al. |
| 6,932,767 B2 | 8/2005 | Landry et al. |
| 7,033,320 B2 | 4/2006 | Von Behren et al. |
| 7,087,023 B2 | 8/2006 | Daft et al. |
| 7,104,956 B1 | 9/2006 | Christopher |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,283,652 B2 | 10/2007 | Mendonca et al. |
| 7,285,094 B2 | 10/2007 | Nohara et al. |
| 7,293,462 B2 | 11/2007 | Lee et al. |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,444,875 B1 | 11/2008 | Wu et al. |
| 7,447,535 B2 | 11/2008 | Lavi |
| 7,448,998 B2 | 11/2008 | Robinson |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,682,311 B2 | 3/2010 | Simopoulos et al. |
| 7,699,776 B2 | 4/2010 | Walker et al. |
| 7,722,541 B2 | 5/2010 | Cai |
| 7,744,532 B2 | 6/2010 | Ustuner et al. |
| 7,750,311 B2 | 7/2010 | Daghighian |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,822,250 B2 | 10/2010 | Yao et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,637 B2 | 7/2011 | Ao et al. |
| 7,984,651 B2 | 7/2011 | Randall et al. |
| 8,002,705 B1 | 8/2011 | Napolitano et al. |
| 8,007,439 B2 | 8/2011 | Specht |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,105,239 B2 | 1/2012 | Specht |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2002/0138003 A1 | 9/2002 | Bukshpan |
| 2002/0161299 A1 | 10/2002 | Prater et al. |
| 2003/0013962 A1 | 1/2003 | Bjaerum et al. |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0054283 A1 | 3/2004 | Corey et al. |
| 2004/0068184 A1 | 4/2004 | Trahey et al. |
| 2004/0100163 A1* | 5/2004 | Baumgartner et al. ....... 310/334 |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236217 A1 | 11/2004 | Cerwin et al. |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0090745 A1 | 4/2005 | Steen |
| 2005/0111846 A1 | 5/2005 | Steinbacher et al. |
| 2005/0113689 A1 | 5/2005 | Gritzky |
| 2005/0113694 A1 | 5/2005 | Haugen et al. |
| 2005/0124883 A1 | 6/2005 | Hunt |
| 2005/0131300 A1 | 6/2005 | Bakircioglu et al. |
| 2005/0147297 A1 | 7/2005 | McLaughlin et al. |
| 2005/0165312 A1 | 7/2005 | Knowles et al. |
| 2005/0203404 A1 | 9/2005 | Freiburger |
| 2005/0215883 A1 | 9/2005 | Hundley et al. |
| 2005/0240125 A1 | 10/2005 | Makin et al. |
| 2005/0252295 A1 | 11/2005 | Fink et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0074320 A1 | 4/2006 | Yoo et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0111634 A1 | 5/2006 | Wu |
| 2006/0122506 A1 | 6/2006 | Davies et al. |
| 2006/0173327 A1 | 8/2006 | Kim |
| 2006/0262291 A1 | 11/2006 | Hess et al. |

(56) References Cited

U.S. PATENT DOCUMENTS

| | | |
|---|---|---|
| 2006/0270934 A1 | 11/2006 | Savord et al. |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |
| 2007/0088213 A1 | 4/2007 | Poland |
| 2007/0138157 A1 | 6/2007 | Dane et al. |
| 2007/0161898 A1 | 7/2007 | Hao et al. |
| 2007/0161904 A1 | 7/2007 | Urbano |
| 2007/0167752 A1 | 7/2007 | Proulx et al. |
| 2007/0167824 A1 | 7/2007 | Lee et al. |
| 2007/0232914 A1 | 10/2007 | Chen et al. |
| 2007/0238985 A1 | 10/2007 | Smith et al. |
| 2007/0242567 A1 | 10/2007 | Daft et al. |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0183075 A1 | 7/2008 | Govari et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269604 A1 | 10/2008 | Boctor et al. |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0287787 A1 | 11/2008 | Sauer et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0099483 A1 | 4/2009 | Rybyanets |
| 2009/0112095 A1 | 4/2009 | Daigle |
| 2009/0131797 A1 | 5/2009 | Jeong et al. |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182233 A1 | 7/2009 | Wodnicki |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1* | 10/2009 | Stribling ............... 600/459 |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069751 A1 | 3/2010 | Hazard et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168566 A1 | 7/2010 | Bercoff et al. |
| 2010/0168578 A1 | 7/2010 | Garson, Jr. et al. |
| 2010/0174194 A1 | 7/2010 | Chiang et al. |
| 2010/0191110 A1 | 7/2010 | Insana et al. |
| 2010/0217124 A1 | 8/2010 | Cooley |
| 2010/0228126 A1 | 9/2010 | Emery et al. |
| 2010/0240994 A1 | 9/2010 | Zheng |
| 2010/0249570 A1 | 9/2010 | Carson et al. |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0268503 A1 | 10/2010 | Specht et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0066030 A1 | 3/2011 | Yao |
| 2011/0098565 A1 | 4/2011 | Masuzawa |
| 2011/0112400 A1 | 5/2011 | Emery et al. |
| 2011/0112404 A1 | 5/2011 | Gourevitch |
| 2011/0125017 A1 | 5/2011 | Ramamurthy et al. |
| 2011/0178400 A1 | 7/2011 | Specht et al. |
| 2011/0201933 A1 | 8/2011 | Specht et al. |
| 2011/0270088 A1 | 11/2011 | Shiina |
| 2011/0301470 A1 | 12/2011 | Sato et al. |
| 2011/0306885 A1 | 12/2011 | Specht |
| 2011/0306886 A1 | 12/2011 | Daft et al. |
| 2011/0319764 A1 | 12/2011 | Okada et al. |
| 2012/0035482 A1 | 2/2012 | Kim et al. |
| 2012/0036934 A1 | 2/2012 | Kröning et al. |
| 2012/0057428 A1 | 3/2012 | Specht et al. |
| 2012/0085173 A1 | 4/2012 | Papadopoulos et al. |
| 2012/0101378 A1 | 4/2012 | Lee |
| 2012/0114210 A1 | 5/2012 | Kim et al. |
| 2012/0121150 A1 | 5/2012 | Murashita |
| 2012/0137778 A1 | 6/2012 | Kitazawa et al. |
| 2012/0141002 A1 | 6/2012 | Urbano et al. |
| 2012/0165670 A1 | 6/2012 | Shi et al. |
| 2012/0179044 A1 | 7/2012 | Chiang et al. |
| 2012/0226201 A1 | 9/2012 | Clark et al. |
| 2012/0277585 A1 | 11/2012 | Koenig et al. |
| 2013/0035595 A1 | 2/2013 | Specht |
| 2013/0070062 A1 | 3/2013 | Fouras et al. |
| 2014/0086014 A1 | 3/2014 | Kobayashi |
| 2014/0243673 A1 | 8/2014 | Anand et al. |

FOREIGN PATENT DOCUMENTS

| | | |
|---|---|---|
| CN | 101190134 A | 6/2008 |
| CN | 101453955 A | 6/2009 |
| CN | 101843501 A | 9/2010 |
| CN | 102018533 A | 4/2011 |
| CN | 102123668 | 7/2011 |
| EP | 1949856 A1 | 7/2008 |
| EP | 2058796 A2 | 5/2009 |
| EP | 2101191 A2 | 9/2009 |

(56) References Cited

FOREIGN PATENT DOCUMENTS

| | | |
|---|---|---|
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2325672 A1 | 5/2011 |
| EP | 2356941 A1 | 8/2011 |
| EP | 1979739 | 10/2011 |
| EP | 2385391 A2 | 11/2011 |
| EP | 2294400 | 2/2012 |
| EP | 2453256 A2 | 5/2012 |
| EP | 1840594 B1 | 6/2012 |
| EP | 1850743 B1 | 12/2012 |
| FR | 2851662 A1 | 8/2004 |
| JP | S49-11189 A | 1/1974 |
| JP | S54-44375 A | 4/1979 |
| JP | S55-103839 A | 8/1980 |
| JP | 57-31848 A | 2/1982 |
| JP | 59-101143 A | 6/1984 |
| JP | S59-174151 A | 10/1984 |
| JP | S60-13109 U | 1/1985 |
| JP | S60-68836 A | 4/1985 |
| JP | 2-501431 A | 5/1990 |
| JP | 03015455 A | 1/1991 |
| JP | 03126443 A | 5/1991 |
| JP | 04017842 A | 1/1992 |
| JP | 4-67856 | 3/1992 |
| JP | 05-042138 A | 2/1993 |
| JP | 6-125908 A | 5/1994 |
| JP | 7-051266 A | 2/1995 |
| JP | 07204201 A | 8/1995 |
| JP | 08154930 A | 6/1996 |
| JP | 08-252253 | 10/1996 |
| JP | 9-103429 A | 4/1997 |
| JP | 9-201361 A | 8/1997 |
| JP | 10-216128 A | 8/1998 |
| JP | 11-089833 A | 4/1999 |
| JP | 11-239578 A | 9/1999 |
| JP | 2001-507794 A | 6/2001 |
| JP | 2001-245884 A | 9/2001 |
| JP | 2002-209894 A | 7/2002 |
| JP | 2002-253548 A | 9/2002 |
| JP | 2002-253549 A | 9/2002 |
| JP | 2004-167092 A | 6/2004 |
| JP | 2004-215987 | 8/2004 |
| JP | 2004-337457 | 12/2004 |
| JP | 2004-351214 | 12/2004 |
| JP | 2005152187 A | 6/2005 |
| JP | 2005-523792 | 8/2005 |
| JP | 2005-526539 | 9/2005 |
| JP | 2006-61203 A | 3/2006 |
| JP | 2006-122657 A | 5/2006 |
| JP | 2006130313 A | 5/2006 |
| JP | 2007-325937 A | 12/2007 |
| JP | 2008-122209 | 5/2008 |
| JP | 2008-513763 A | 5/2008 |
| JP | 2008132342 A | 6/2008 |
| JP | 2008522642 A | 7/2008 |
| JP | 2008-259541 A | 10/2008 |
| JP | 2008279274 A | 11/2008 |
| JP | 2009240667 A | 10/2009 |
| JP | 20105375 | 1/2010 |
| JP | 2010124842 A | 6/2010 |
| JP | 2010526626 A | 8/2010 |
| KR | 100715132 B | 4/2007 |
| KR | 1020090103408 A | 10/2009 |
| WO | WO 92/18054 A1 | 10/1992 |
| WO | WO 98/00719 A2 | 1/1998 |
| WO | WO01/64109 A1 | 9/2001 |
| WO | WO02/084594 A2 | 10/2002 |
| WO | WO2005/009245 A1 | 2/2005 |
| WO | WO 2006/114735 A1 | 11/2006 |
| WO | WO 2007/127147 A2 | 11/2007 |
| WO | WO2009/060182 A2 | 5/2009 |
| WO | WO 2010/017445 A2 | 2/2010 |
| WO | WO 2010/095094 A1 | 8/2010 |
| WO | WO2010/139519 A1 | 12/2010 |
| WO | WO2011/004661 A1 | 1/2011 |
| WO | WO2011/057252 A1 | 5/2011 |
| WO | WO2011/064688 A1 | 6/2011 |
| WO | WO2011/100697 A1 | 8/2011 |
| WO | WO2011/123529 A1 | 10/2011 |
| WO | WO2012/028896 A1 | 3/2012 |
| WO | WO2012/049124 A2 | 4/2012 |
| WO | WO2012/049612 A2 | 4/2012 |
| WO | WO2012/078639 A1 | 6/2012 |
| WO | WO2012/091280 A1 | 7/2012 |
| WO | WO2012/160541 A2 | 11/2012 |

OTHER PUBLICATIONS

Cristianini et al.; An Introduction to Support Vector Machines; Cambridge University Press; pp. 93-111; Mar. 2000.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 428, 484; Feb. 1994.

Haykin, Simon; Neural Networks: A Comprehensive Foundation (2nd Ed.); Prentice Hall; pp. 156-187; Jul. 16, 1998.

Ledesma-Carbayo et al.; Spatio-temporal nonrigid registration for ultrasound cardiac motion estimation; IEEE Trans. on Medical Imaging; vol. 24; No. 9; Sep. 2005.

Leotta et al.; Quantitative three-dimensional echocardiography by rapid imaging . . . ; J American Society of Echocardiography; vol. 10; No. 8; ppl 830-839; Oct. 1997.

Morrison et al.; A probabilistic neural network based image segmentation network for magnetic resonance images; Proc. Conf. Neural Networks; Baltimore, MD; vol. 3; pp. 60-65; Jun. 1992.

Nadkarni et al.; Cardiac motion synchronization for 3D cardiac ultrasound imaging; Ph.D. Dissertation, University of Western Ontario; Jun. 2002.

Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.

Sakas et al.; Preprocessing and volume rendering of 3D ultrasonic data; IEEE Computer Graphics and Applications; pp. 47-54, Jul. 1995.

Sapia et al.; Ultrasound image deconvolution using adaptive inverse filtering; 12 IEEE Symposium on Computer-Based Medical Systems, CBMS, pp. 248-253; Jun. 1999.

Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.

Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.

Specht et al.; Deconvolution techniques for digital longitudinal tomography; SPIE; vol. 454; presented at Application of Optical Instrumentation in Medicine XII; pp. 319-325; Jun. 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. on Neural Networks; vol. 2.; No. 6; Nov. 1991.

Specht, D.F.; Blind deconvolution of motion blur using LMS inverse filtering; Lockheed Independent Research (unpublished); Jun. 23, 1975.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; Feb. 1990.

(56) References Cited

OTHER PUBLICATIONS

Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Specht, Donald F.; U.S. Appl. No. 13/333,611 entitled "Method and Apparatus to Visualize the Coronary Arteries Using Ultrasound," filed Dec. 21, 2011.
Smith et al.; U.S. Appl. No. 13/272,105 entitled "Concave Ultrasound Transducers and 3D Arrays," filed Oct. 12, 2011.
Kramb et al.,; Considerations for using phased array ultrasonics in a fully automated inspection system. Review of Quantitative Nondestructive Evaluation, vol. 23, ed. D. O. Thompson and D. E. Chimenti, pp. 817-825, (month unavailable) 2004.
Specht et al.; U.S. Appl. No. 13/690,989 entitled "Motion Detection Using Ping-Based and Multiple Aperture Doppler Ultrasound," filed Nov. 30, 2012.
Brewer et al.; U.S. Appl. No. 13/730,346 entitled "M-Mode Ultrasound Imaging of Arbitrary Paths," filed Dec. 28, 2012.
Specht et al.; U.S. Appl. No. 13/773,340 entitled "Determining Material Stiffness Using Multiple Aperture Ultrasound," filed Feb. 21, 2013.
Hendee et al.; Medical Imaging Physics; Wiley-Liss, Inc. 4th Edition; Chap. 19-22; pp. 303-353; © 2002 (year of pub. sufficiently earlier than effective US filed and any foreign priority date).
Wikipedia; Point cloud; 2 pages; Nov. 24, 2014; retrieved from the internet (https://en.wikipedia.org/w/index.php?title=Point_cloud &oldid=472583138).
Li et al.; An efficient speckle tracking algorithm for ultrasonic imaging; 24; pp. 215-228; Oct. 1, 2002.
UCLA Academic Technology; SPSS learning module: How can I analyze a subset of my data; 6 pages; retrieved from the internet (http://www.ats.ucla.edu/stat/spss/modules/subset_analyze.htm) Nov. 26, 2001.
Wikipedia; Curve fitting; 5 pages; retrieved from the internet (http: en.wikipedia.org/wiki/Curve_fitting) Dec. 19, 2010.
Wikipedia; Speed of sound; 17 pages; retrieved from the internet (http: en.wikipedia.org/wiki/Speed_of_sound) Feb. 15, 2011.
Abeysekera et al.; Alignment and calibration of dual ultrasound transducers using a wedge phantom; Ultrasound in Medicine and Biology; 37(2); pp. 271-279; Feb. 2011.
Carson et al.; Measurement of photoacoustic transducer position by robotic source placement and nonlinear parameter estimation; Biomedical Optics (BiOS); International Society for Optics and Photonics (9th Conf. on Biomedical Thermoacoustics, Optoacoustics, and Acousto-optics; vol. 6856; 9 pages; Feb. 28, 2008.
Chen et al.; Maximum-likelihood source localization and unknown sensor location estimation for wideband signals in the near-field; IEEE Transactions on Signal Processing; 50(8); pp. 1843-1854; Aug. 2002.
Chen et al.; Source localization and tracking of a wideband source using a randomly distributed beamforming sensor array; International Journal of High Performance Computing Applications; 16(3); pp. 259-272; Fall 2002.
Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.
Gazor et al.; Wideband multi-source beamforming with array location calibration and direction finding; Conference on Acoustics, Speech and Signal Processing ICASSP-95; Detroit, MI; vol. 3 IEEE; pp. 1904-1907; May 9-12, 1995.
Heikkila et al.; A four-step camera calibration procedure with implicit image correction; Proceedings IEEE Computer Scociety Conference on Computer Vision and Pattern Recognition; San Juan; pp. 1106-1112; Jun. 17-19, 1997.
Hsu et al.; Real-time freehand 3D ultrasound calibration; CUED/F-INFENG/TR 565; Department of Engineering, University of Cambridge, United Kingdom; 14 pages; Sep. 2006.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Slavine et al.; Construction, calibration and evaluation of a tissue phantom with reproducible optical properties for investigations in light emission tomography; Engineering in Medicine and Biology Workshop; Dallas, TX; IEEE pp. 122-125; Nov. 11-12, 2007.
Urban et al; Implementation of vibro-acoustography on a clinical ultrasound system; IEEE Transactions on Ultrasonics, Ferroelectrics, and Frequency Control; 58(6); pp. 1169-1181; Jun. 2011 (Author Manuscript).
Urban et al; Implementation of vibro-acoustography on a clinical ultrasound system; IEEE Ultrasonics Symposium (IUS); pp. 326-329; Oct. 14, 2010.
Wang et al.; Photoacoustic tomography of biological tissues with high cross-section resolution: reconstruction and experiment; Medical Physics; 29(12); pp. 2799-2805; Dec. 2002.
Yang et al.; Time-of-arrival calibration for improving the microwave breast cancer imaging; 2011 IEEE Topical Conf. on Biomedical Wireless Technologies, Networks, and sensing Systems (BioWireleSS); Phoenix, AZ; pp. 67-70; Jan. 16-19, 2011.
Opretzka et al.; A high-frequency ultrasound imaging system combining limited-angle spatial compounding and model-based synthetic aperture focusing; IEEE Transactions on Ultrasonics, Ferroelectrics and Frequency Control, IEEE, US; 58(7); pp. 1355-1365; Jul. 2, 2011.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Arigovindan et al.; Full motion and flow field recovery from echo doppler data; IEEE Transactions on Medical Imaging; 26(1); pp. 31-45; Jan. 2007.
Capineri et al.; A doppler system for dynamic vector velocity maps; Ultrasound in Medicine & Biology; 28(2); pp. 237-248; Feb. 28, 2002.
Dunmire et al.; A brief history of vector doppler; Medical Imaging 2001; International Society for Optics and Photonics; pp. 200-214; May 30, 2001.
Saad et al.; Computer vision approach for ultrasound doppler angle estimation; Journal of Digital Imaging; 22(6); pp. 681-688; Dec. 1, 2009.
Zang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.

\* cited by examiner 1, 1.5, and 2 D Implementation using CMUT Material

Variable Cardiac Implementation

Fixed Cardiac Implementation

Omniplane Style TEE Implementation FIG. 9
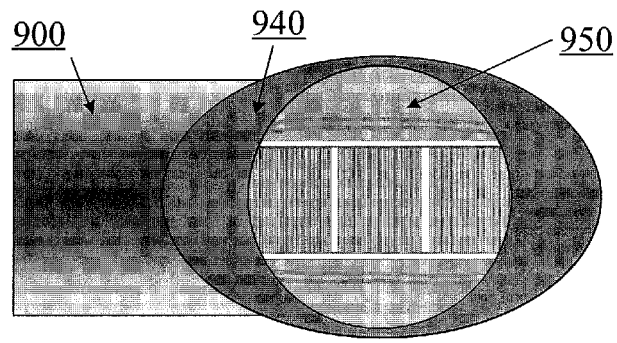
FIG. 9A
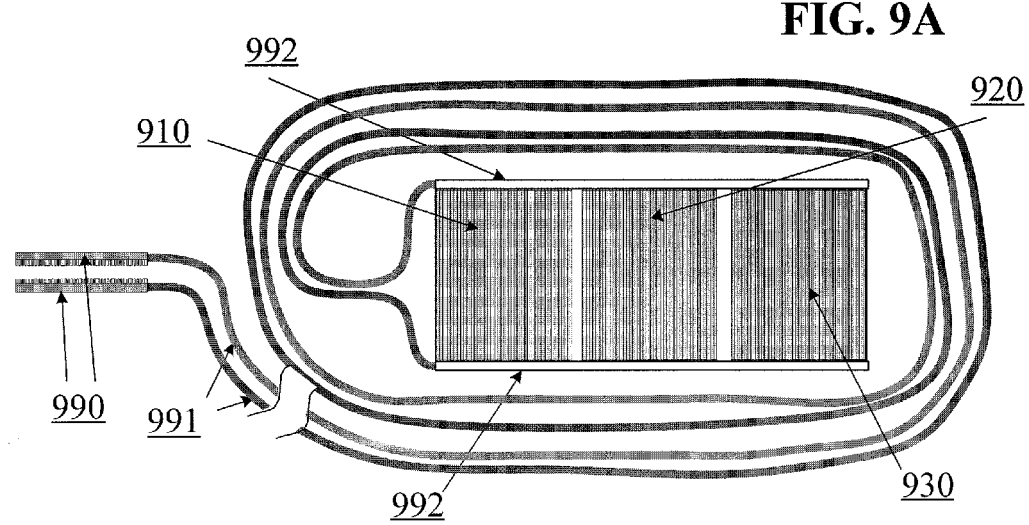
FIG. 9B
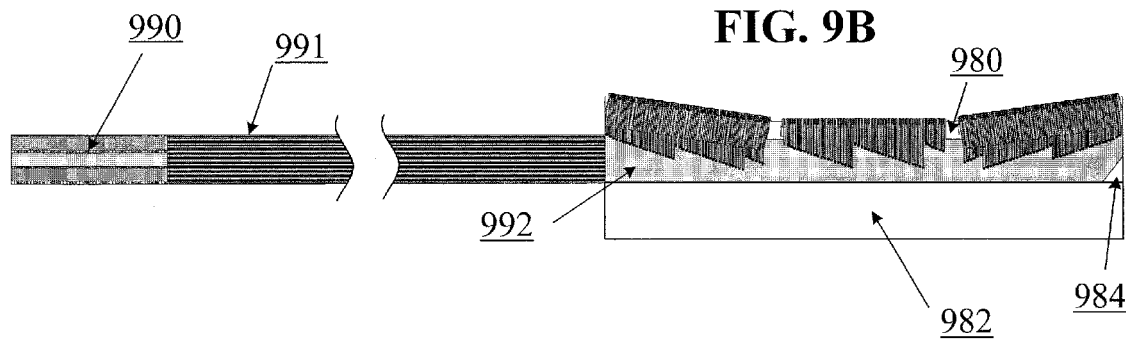

Intracavity Probe Implementation

IVUS Probe Implementation

**MAUI 1 D Implementation using
multiple Piezoelectric arrays**

MULTIPLE APERTURE PROBE INTERNAL APPARATUS AND CABLE ASSEMBLIES

CROSS REFERENCE TO RELATED APPLICATIONS

This application claims the benefit of U.S. Provisional Patent Application No. 61/392,841, filed Oct. 13, 2010, titled "MULTI APERTURE CABLE ASSEMBLY FOR MULTIPLE APERTURE PROBE FOR USE IN MEDICAL ULTRASOUND", which application is incorporated herein by reference in its entirety.

This application is related to U.S. Pat. No. 8,007,439, issued Aug. 30, 2011, titled "Method and Apparatus to Produce Ultrasonic Images Using Multiple Apertures", U.S. patent application Ser. No. 12/760,375, filed Apr. 14, 2010, titled "Universal Multiple Aperture Medical Ultrasound Probe", U.S. patent application Ser. No. 13/002,778, filed Aug. 7, 2009, titled "Imaging With Multiple Aperture Medical Ultrasound and Synchronization of Add-On Systems", U.S. patent application Ser. No. 12/760,327, filed Apr. 14, 2010, titled "Multiple Aperture Ultrasound Array Alignment Fixture," and U.S. patent application Ser. No. 12/760,375, filed Apr. 14, 2010, titled "Universal Multiple Aperture Medical Ultrasound Transducer".

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to imaging techniques, and more particularly to ultrasound imaging techniques, and still more particularly to an apparatus for producing ultrasonic images using multiple apertures.

BACKGROUND

In conventional ultrasonic imaging, a focused beam of ultrasound energy is transmitted into body tissues to be examined and the returned echoes are detected and plotted to form an image.

In order to insonify the body tissues, a beam formed either by a phased array or a shaped transducer is scanned over the tissues to be examined. Traditionally, the same transducer or array is used to detect the returning echoes. This design configuration lies at the heart of one of the most significant limitations in the use of ultrasonic imaging for medical purposes; namely, poor lateral resolution. Theoretically the lateral resolution could be improved by increasing the aperture of the ultrasonic probe, but the practical problems involved with aperture size increase have kept apertures small and lateral resolution large. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use (e.g. intracavity or intravenous), the limitation on aperture size is a serious limitation as well. The problem is that it is difficult to keep the elements of a large aperture array in phase because the speed of ultrasound transmission varies with the type of tissue between the probe and the area of interest. According to Wells (*Biomedical Ultrasonics*, as cited above), the transmission speed varies up to plus or minus 10% within the soft tissues. When the aperture is kept small, the intervening tissue is, to a first order of approximation, all the same and any variation is ignored. When the size of the aperture is increased to improve the lateral resolution, the additional elements of a phased array may be out of phase and may actually degrade the image rather than improving it.

With single aperture transducers, it has been commonly assumed that the beam paths used by the elements of the transducer are close enough together to be considered similar in tissue density profile, and therefore no compensation was necessary. The use of this assumption, however, severely limits the size of the aperture that can be used.

SUMMARY

Multiple aperture ultrasound probes may be constructed with unique cable assemblies, multiple flex connectors, and unique backing plate constructions, and unique electrical connections to reduce noise and improve the quality of images produced using multiple aperture ultrasound imaging techniques. The embodiments provided herein allow for effective mechanical and electrical connection of ultrasound transducer elements and arrays to probes and imaging control electronics.

In one embodiment, a multiple aperture ultrasound probe is provided, comprising a probe housing containing a first ultrasound array and a second ultrasound array, a first flex circuit connected to the first ultrasound array, a second flex circuit connected to the second ultrasound array, a backing plate configured to secure the first and second ultrasound arrays in predetermined positions and orientations relative to one another, a first coaxial cable group electrically connected to the first flex circuit, a second coaxial cable group electrically connected to the second flex circuit, and a flex/PC board comprising flex connectors and an array of terminals, wherein said flex connectors are connected to said first and second flex circuits, and wherein said terminals are connected to said first and second coaxial cable groups.

In some embodiments, the first and second ultrasound arrays comprise a plurality of transducer elements, wherein each element is connected to the flex/PC board with a differential pair of conductors having a signal ground separated from a chassis ground.

In one embodiment, the backing plate is electrically connected to chassis grounding circuitry via the transducer cable shield originating at an electronic control system. In another embodiment, the backing plate internally supports the probe structure.

In some embodiments, the multiple aperture ultrasound probe further comprises a calibration chip mounted on the flex/PC board. In some embodiments, the calibration chip is configured to store position and orientation information about the first and second ultrasound arrays.

In some embodiments, the multiple aperture ultrasound probe further comprises a probe position sensor mounted on the flex/PC board.

In another embodiment, the multiple aperture ultrasound probe further comprise a synchronization module mounted on the flex/pc board, the synchronization module being configured to synchronize an add-on ultrasound device with the first and second ultrasound arrays.

In one embodiment, the multiple aperture ultrasound probe further comprises a third ultrasound array secured to the backing plate, a third flex circuit connected to the third ultrasound array, a third coaxial cable group electrically connected to the third flex circuit, wherein flex connectors of the flex/PC board are connected to the third flex circuit and terminals of the flex/PC board are connected to the third cable group.

In one embodiment, the flex/PC board comprises a probe chassis ground circuit that is electrically connected to a shielding element surrounding a section of the first and second cable group bundles between the probe housing and a distal connector.

In another embodiment, at least one of the first array and the second array comprises an internal flex cabling configured to accommodate movement of the first ultrasound array away from the second ultrasound array.

In some embodiments, the probe further comprises a sliding portion configured to allow the first ultrasound array and the second ultrasound array to move laterally relative to the probe housing.

In one embodiment, at least one of the first ultrasound array and the second ultrasound array is configured to rotate about an axis of the probe housing.

In additional embodiments, the probe housing further comprises a lever configured to move the first ultrasound array or the second ultrasound array relative to the probe housing.

In some embodiments, the probe housing further comprising a dial and an electric motor configured to move the first ultrasound array or the second ultrasound array relative to the probe housing.

BRIEF DESCRIPTION OF THE FIGURES

FIG. 9 illustrates an embodiment of a multiple aperture omniplane transesophogeal (TEE) multiple aperture probe using three or more arrays.

FIG. 9A is a top view of the arrays of the probe of FIG. 9, including associated cabling without the encasement.

FIG. 9B illustrates a side view of the probe of FIG. 9 multiple aperture illustrating individual arrays secured by a backing plate.

FIG. 12A illustrates a side view of an embodiment of a multiple aperture probe with five arrays.

DETAILED DESCRIPTION

Multiple aperture ultrasound imaging probes may be substantially improved by providing unique cable assemblies, flex connectors, and backing blocks and other components to improve ultrasound signal quality and overall imaging performance. For example, unique backing blocks may be configured to maintain a desired geometry between adjacent elements and arrays that may not be attached to each other via a common substrate. Further, some embodiments of common substrates may be shaped in such a way that additional mechanical support systems provide substantial benefits. Systems and methods for effectively connecting ultrasound transducer elements and arrays both mechanically and electronically in multiple aperture probes are shown and described herein.

Embodiments of multiple aperture ultrasound imaging (MAUI) probes and methods of using them to obtain high resolution ultrasound images are shown and described in Applicants' prior US patent applications, which are referenced above.

Figure 2:
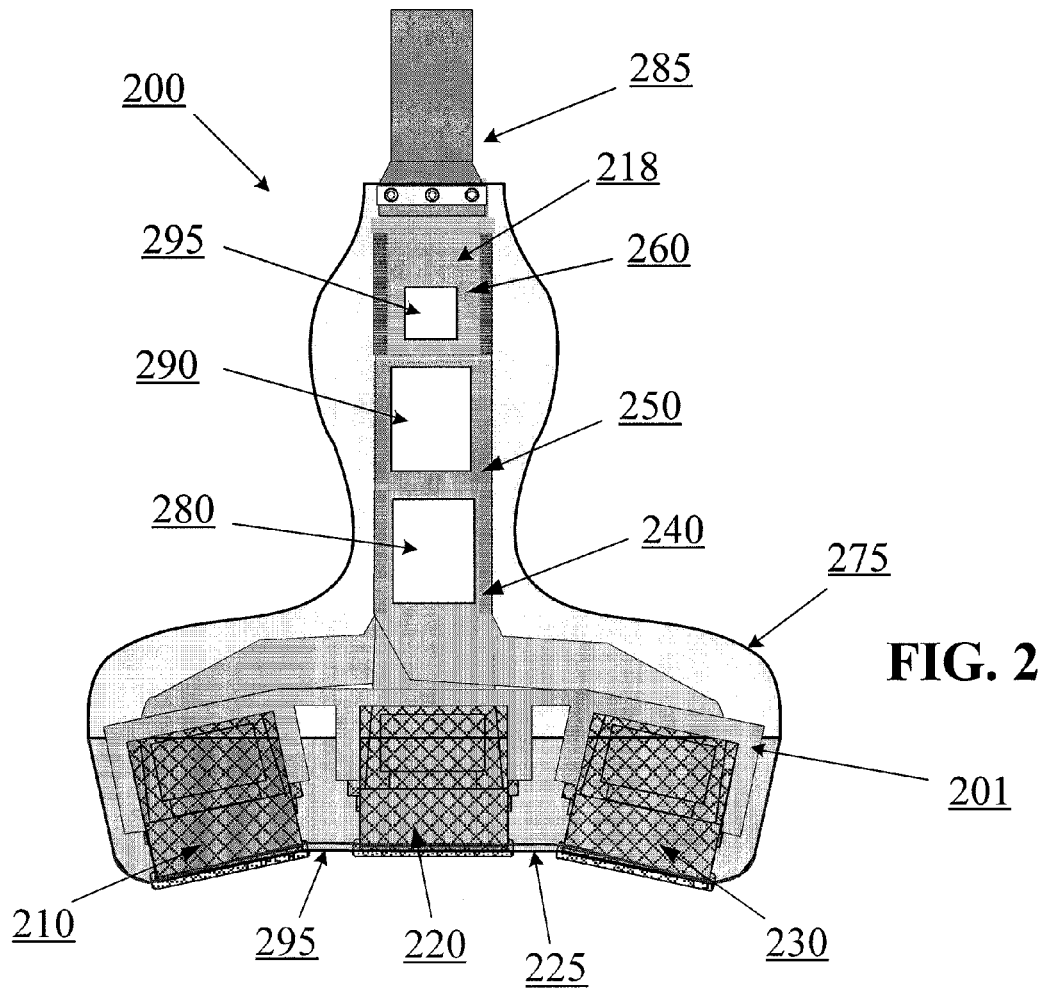
FIG. 2 is an elevation view of one embodiment of a multiple aperture ultrasound probe with a top housing section removed to reveal components therein.
Figure 7:
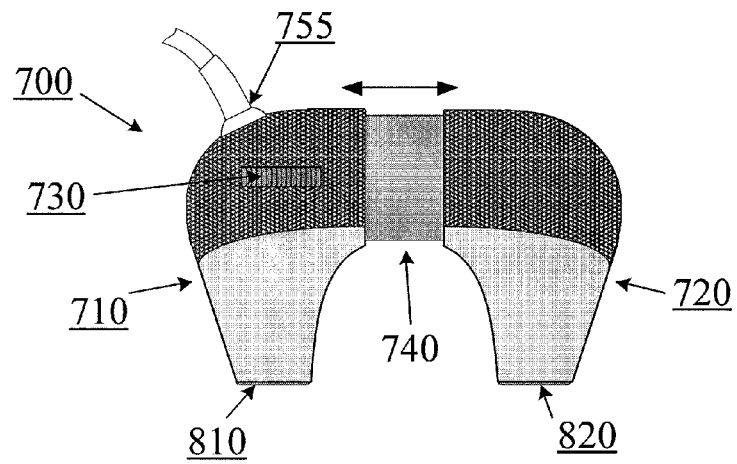
FIG. 7 illustrates an embodiment of an adjustable, extendable two-array multiple aperture probe in a partially extended configuration.
Figure 7A:
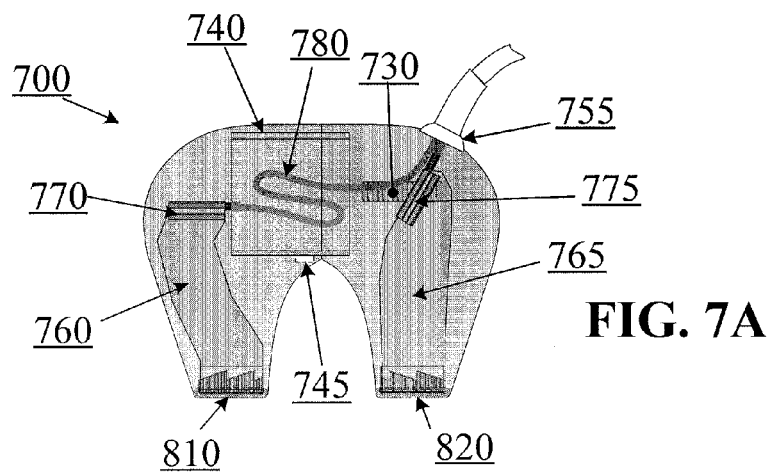
FIG. 7A is a side view of the probe of FIG. 7 in a collapsed configuration with internal components visible.

As described in the above-referenced patents and applications, the structure of a MAUI Probe can vary substantially to meet the needs of a particular application. For example, a general radiology probe (an embodiment of which is shown in FIG. 2) may contain multiple arrays that maintain separate physical points of contact with the patient's skin, allowing multiple physical imaging apertures. A cardiac probe (an embodiment of which is shown in FIG. 7) may contain as few as two arrays allowing the probe to fit simultaneously between two or more intercostal spaces. An intracavity version of a MAUI probe (an embodiment of which is shown in FIGS. 9-9B), may have arrays positioned along the length of a wand, while an intravenous MAUI probe (an embodiment of which is shown in FIG. 13) may allow the arrays to be located on the distal length the catheter and separated by mere millimeters. In each of these application-specific probe embodiments, a plurality of transducer arrays may be positioned and contained by a single backing plate configured to support each of the arrays in a desired position at a desired specified angle relative to the other arrays of the probe. Details of the angle and position of probes may depend on the intended function of a probe.

As used herein the terms "ultrasound transducer" and "transducer" may carry their ordinary meanings as understood by those skilled in the art of ultrasound imaging technologies, and may refer without limitation to any component capable of converting an electrical signal into an ultrasonic signal and/or vice versa. For example, in some embodiments, an ultrasound transducer may comprise a piezoelectric device. In other embodiments, ultrasound transducers may comprise capacitive micromachined ultrasound transducers (CMUT).

Ultrasound transducers are often configured in arrays of multiple individual transducer elements. As used herein, the terms "transducer array" or "array" generally refers to a collection of transducer elements mounted to a common substrate. Such arrays may have one dimension (1D), two dimensions (2D), 1.5 dimensions (1.5D) as understood by those skilled in the art. Other dimensioned arrays as understood by those skilled in the art may also be used. Transducer arrays may be made from piezoelectric materials, CMUT materials or any other suitable material. An element of a transducer array may be the smallest discretely functional component of an array. For example, in the case of an array of piezoelectric transducer elements, a single element may be a single piezoelectric crystal or a single machined section of a piezoelectric crystal. A transducer array may include any number of individual transducer elements as needed. Thus, in some embodiments an array may include a single element, and in other embodiments an array my include hundreds of elements. Unless specified otherwise for a particular embodiment, the embodiments herein may use any suitable ultrasound transducer array.

As used herein, the term "aperture" refers to a conceptual "opening" through which ultrasound signals may be sent and/or received. In actual practice, an aperture is simply a group of transducer elements that are collectively managed as a common group by imaging control electronics. For example, in some embodiments an aperture may be a physical grouping of elements which may be physically separated from elements of an adjacent aperture. For example, each of the three transducer arrays in the probe of FIG. 2 may be treated as a separate aperture. However, adjacent apertures need not necessarily be physically separated.

In some embodiments, two apertures may be located adjacent one another on a continuous array. In other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below.

Figure 1:
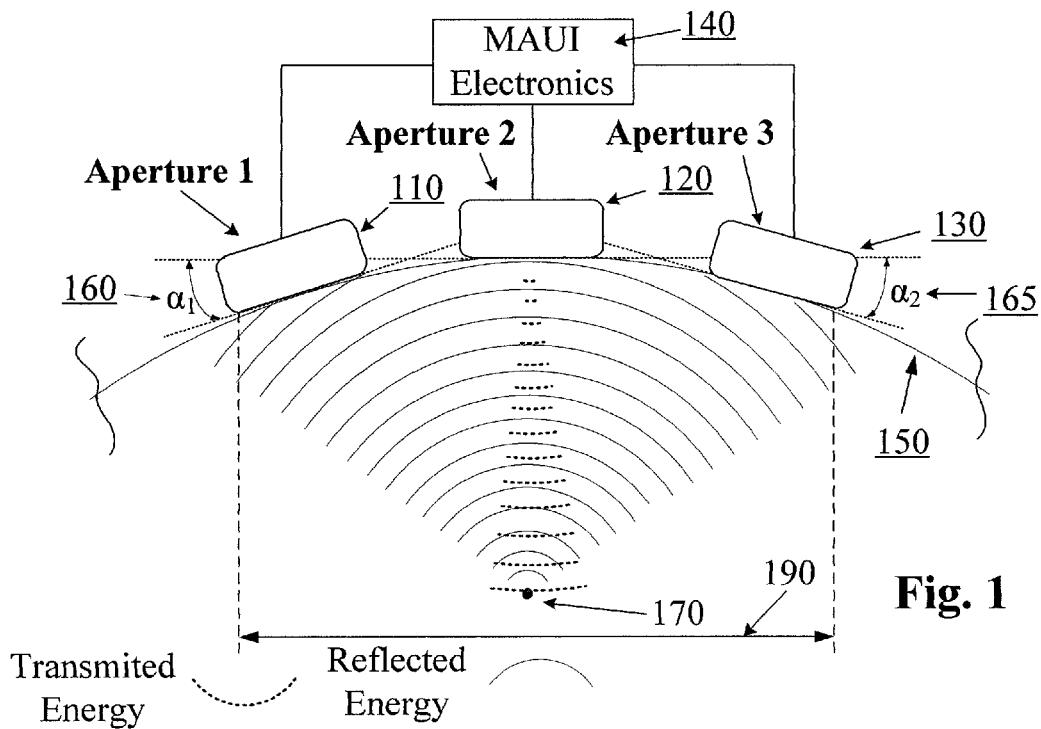
FIG. 1 is a block diagram illustrating one embodiment of transmit and receive functions of a Multiple Aperture Ultrasound Imaging (MAUI) probe.
Figure 1A:
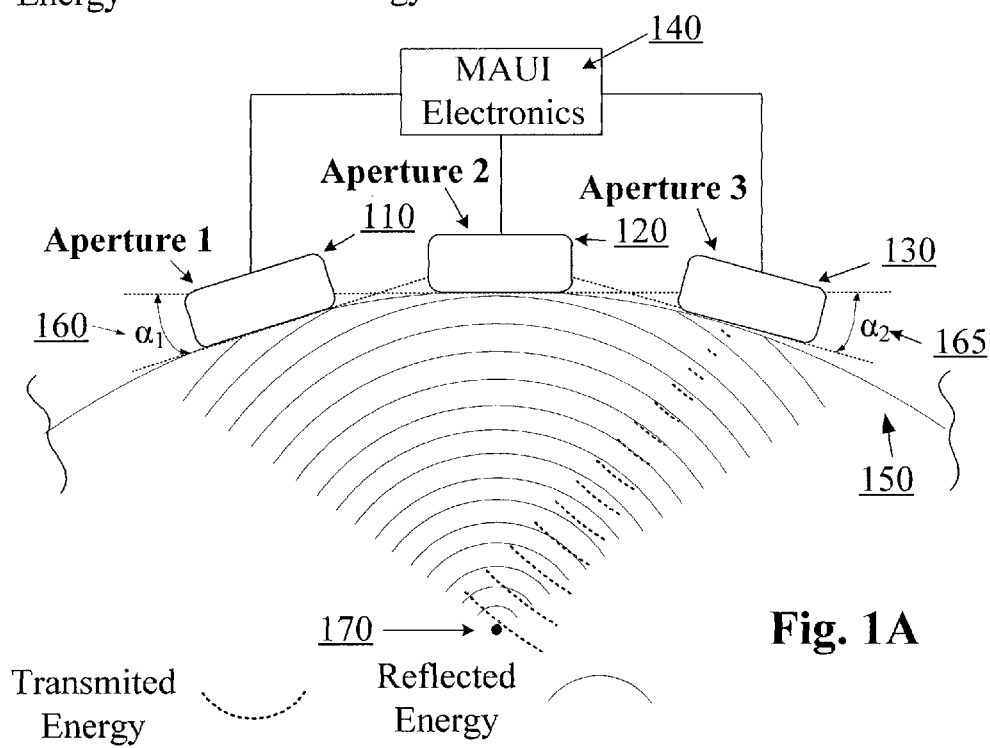
FIG. 1A is a block diagram illustrating additional functions of a multiple aperture ultrasound imaging system.

FIGS. 1 and 1A provide schematic illustrations of a multiple aperture ultrasound imaging process. Control electronics 140 may be provided to control the physical function of elements located within the different apertures 110, 120, and 130 of a Multiple Aperture Ultrasound Probe. FIGS. 1 and 1A demonstrate that in some embodiments, transmissions from two different apertures 120 in FIGS. 1 and 130 in FIG. 2 can be used to illuminate a target 170, while elements in all apertures 110, 120 and 130 can all be used for receive beamforming.

In some embodiments, a multiple aperture ultrasound imaging probe may be calibrated to precisely determine the acoustic position of each transducer element of each array. Embodiments of systems and methods for calibrating an ultrasound probe are provided in U.S. patent application Ser. No. 12/760,327. Thus, while calibration may allow for the use of complex arrays and probes (including adjustable probes), it is desirable that the transducer elements and arrays remain in the same physical position between calibration and use of a probe.

Some embodiments of multiple aperture ultrasound probes have several of the distinguishing features illustrated in FIG. 2. For example, the probe 200 of FIG. 2 includes three transducer arrays 210, 220 and 230, which are physically separated from one another and oriented at different "look angles" with respect to a region of interest to be imaged. While the probe 200 of FIG. 2 includes three transducer arrays, the features and advantages of the embodiments herein may be realized with probes having any number of independent transducer arrays, including arrays with non-planar shapes.

Figure 4:
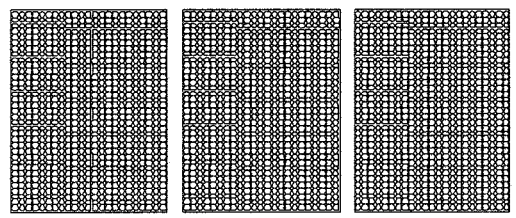
FIG. 4 illustrates an embodiment of 1D, 1.5d or 2D arrays for use in a 3-array multiple aperture ultrasound probe.
Figure 4:
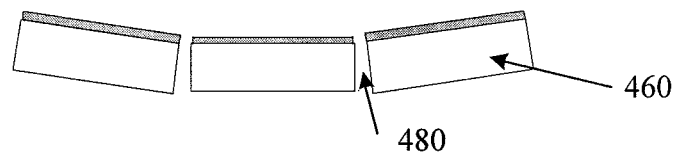
Figure 4A:
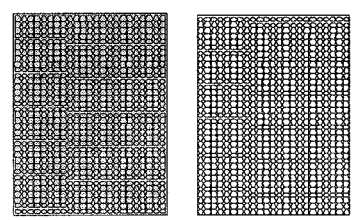
FIG. 4A illustrates an embodiment of a 2-array multiple aperture transducer array.
Figure 4A:
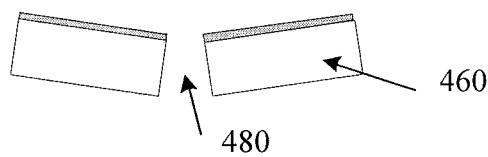

In some embodiments, each array may be constructed with a separate substrate or backing block (e.g. see 460 in FIGS. 4 and 4A). The backing block may be configured to structurally support the elements of an array in a desired shape (e.g., a planar shape). Backing blocks may be made of any substantially rigid material, such as metals, plastics, ceramics, etc. In some embodiments, a probe with multiple arrays may include arrays that all have the same shape and dimensions. In other embodiments, a probe with multiple arrays may include arrays that all have different shapes and/or dimensions. For example, one or more arrays in a multiple-array probe may be circular, elliptical, oblong, rectangular, square, polygonal or other symmetrical or asymmetrical shapes. In some embodiments, a probe with multiple arrays may include one or more arrays that are entirely or partially configured to transmit and/or receive ultrasound signals of a different frequency than other arrays in the probe.

Spacing between arrays (e.g., see 480 in FIGS. 4 and 4A) may vary, and need not be evenly distributed across a probe. In some embodiments, arrays may be arranged symmetrically or asymmetrically in a probe.

Referring back to FIG. 2, a probe may also include a transmit synchronization module 280 for identifying the start of pulse in certain applications. In some embodiments, a probe displacement sensor 290 may also be included within a probe housing. In some embodiments, the probe displacement sensor 290 may be an accelerometer or gyroscope configured to sense the three dimensional movement of the probe. In some embodiments, a calibration chip 295 may also be provided in the probe housing. In further embodiments, additional electrical or electronic components may also be included within the probe housing.

In some embodiments, a plurality of arrays within a single probe, such as the three arrays 210, 220, 230 in the probe of FIG. 2, may share a common backing plate 201 that is configured to secure the arrays in a designed position and orientation relative to one another and relative to the probe housing.

In the embodiment of FIG. 1, the angle $\alpha_1$ 160 is the angle between a line parallel to the elements of the left array 110 and an intersecting line parallel to the elements of the center array 120. Similarly, the angle $\alpha_2$ 165 is the angle between a line parallel to the elements of the right array 130 and an intersecting line parallel to the elements of the center array 120. Angle $\alpha_1$ and angle $\alpha_2$ need not be equal. In some embodiments, there are benefits in achieving optimum beamforming if the two angles 160, 165 are nearly equal.

FIG. 2 illustrates an embodiment of a MAUI probe 200 having three transducer arrays mounted in a housing 275 at static or pre-set mechanical positions and angles relative to one another and relative to the probe housing 275. The lateral arrays 210, 230 may be fixed at a desired position and angle, $\alpha$, relative to the central array 220 by attaching all three arrays 210, 220, 230 onto a single backing plate 201.

In some embodiments, as shown in FIG. 2 for example, the lateral arrays 210, 230 may both be positioned at an angle $\alpha$ of about 12.5° relative to the central array 220. In some embodiments, the angle $\alpha$ may be varied in order to optimize a probe for a particular imaging application. In other embodiments, the angle $\alpha$ of one or both lateral arrays relative to a central array may vary within a range of values to optimize imaging performance at different depths.

For a scatterer at a given depth, the effective aperture of a substantially planar lateral array is proportional to the sine of the angle between a line from the scatterer to the center of the lateral array and a line on the surface of the array itself. For example, with the lateral arrays positioned at an angle $\alpha$ of about 12.5°, the effective aperture of the lateral sub arrays is optimized at a depth of about 10 cm from the tissue surface, which may be beneficial when imaging cardiac features. Thus, in some embodiments, the angle $\alpha$ may be chosen as the best compromise for tissues at a desired depth range.

Figure 2A:
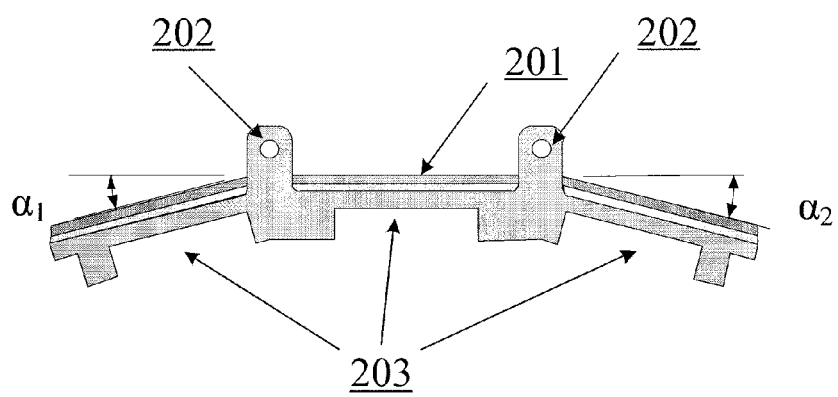
FIG. 2A illustrates one embodiment of a backing plate for securing multiple transducer arrays in predetermined positions and orientations with respect to each other within the probe housing.

FIG. 2A illustrates an embodiment of a backing plate 201 which may be used to mount three arrays into a multiple aperture ultrasound probe housing, such as that shown in FIG. 2. In some embodiments, the backing block may be configured to support lateral transducer arrays at an angle $\alpha$ relative to the central array. In some embodiments, the backing plate 210 may include slots 203 for receiving and retaining the backing blocks 460 of transducer arrays.

The backing plate 201 may be constructed by any suitable manufacturing process including machining, stamping, forging, casting, molding, 3D printing, etc. In some embodiments, the backing plate 201 may be constructed with sufficiently strict tolerances that array backing blocks fit snugly within the slots 203. In some embodiments, array backing blocks may be secured to the backing plate 201 with mechanical fasteners, adhesives, press fits or any other suitable method.

In some embodiments, transducer arrays may be manufactured with electrical contacts exposed on one or more side surfaces of the array and/or backing block material. A flex circuit may be electrically connected to those contacts. In such embodiments, the backing plate 201 may be configured to leave such array electrical contacts exposed so as to allow flex circuits to be electrically connected to the arrays. For example, the backing plate 201 may include one or more slots, channels or openings to accommodate such electrical connections. In other embodiments, a backing plate 201 may include one or more connectors configured to electrically connect array elements to corresponding flex circuit conductors while keeping the array element connections insulated from the backing block.

In some embodiments, the backing plate 201 may include one or more ribs in order to provide additional mechanical rigidity without necessarily adding weight to the probe. The backing plate 201 may also include any number of mounting flanges 202 or other structures configured to allow the backing plate 201 to be secured to one or more probe housing components. In some embodiments, the backing plate 201 may be secured to a probe housing shell 175 with mechanical fasteners, adhesives, press fits, or other methods. In some embodiments, a backing plate 201 may be formed integrally with a probe housing component.

In some embodiments, the backing plate 201 may also be used to complete a separate electrical grounding circuit, which will be referred to herein as a chassis ground. A chassis ground circuit, which will be discussed in more detail below, may extend from the backing plate, through a cable, through a connector and to an ultrasound imaging control/display system.

Figure 2B:
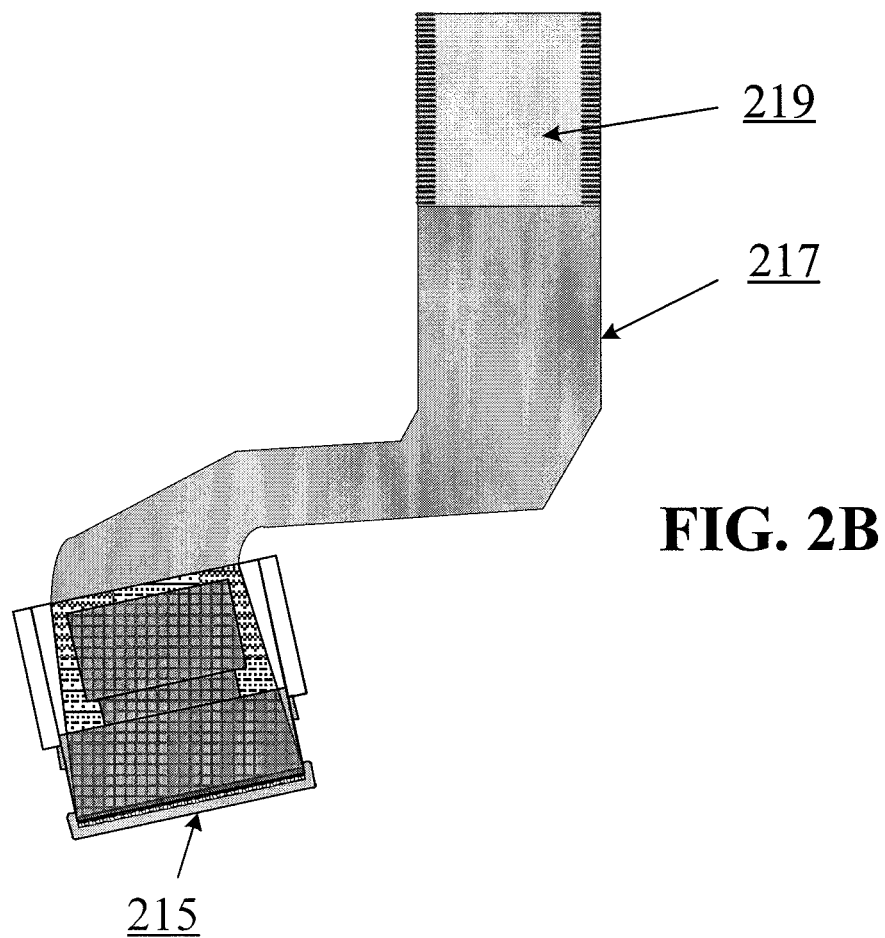
FIG. 2B is a diagram of one embodiment of a flex circuit attaching directly to an ultrasound transducer array.

In some embodiments, as shown in FIG. 2B, a lens 215 may be provided at a front surface of each transducer array. In some embodiments, a second common lens may be provided in front of each of the multiple arrays. In some embodiments, the individual lenses, or a single common lens may form a seal with the probe housing 275 to prevent coupling gel or other liquids from getting inside of the probe. In some embodiments, the front surfaces of the lenses of arrays 210, 220, and 230 may combine with the probe encasement 275 to form a substantially continuous concave arc.

In some embodiments, a multiple aperture ultrasound probe 200 may be a handheld apparatus that operates at a location remote from a base unit system configured to send and receive ultrasound signals. In some embodiments, communication between a multiple aperture probe and a base unit system may be performed through a cable that both mechanically and electrically connects the probe to a base unit system (or systems) configured to send and receive ultrasound signals. In some embodiments, it is advantageous to provide separate cabling and connections to each of the arrays or individual elements within a probe assembly.

Figure 3:
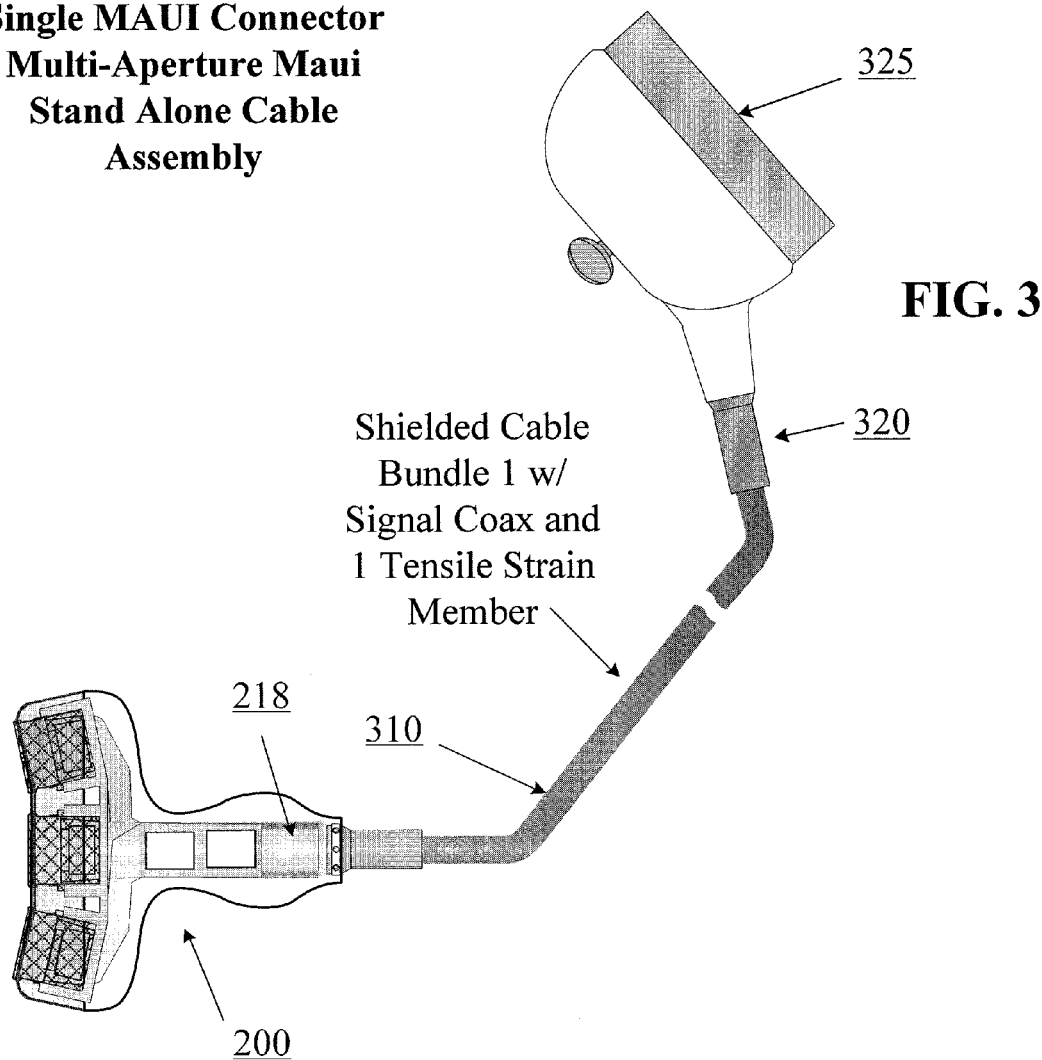
FIG. 3 illustrates an embodiment of a multiple aperture probe, cable and connector assembly.

FIG. 3 illustrates a multiple aperture ultrasound probe 200 including a cable 310 and connector 325. In some embodiments, strain relief elements 320 may be provided at junctions where the cable 310 connects to the connector housing and the probe housing. In some embodiments, the cable 310 is electrically connected to a flex/PC board 218 (examples of such connections are discussed below with reference to FIG.

2D). In some embodiments, the cable 310 may comprise a shielded construction in which a continuous conductor (e.g. a braid or thin foil) surrounds a bundle of individual conductors.

In some embodiments, the bundle of conductors may include a plurality of coaxial cables, which are themselves individually shielded. In some embodiments, the cable bundle may also include coaxial conductors that may be electrically connected to additional electronic components within the probe housing, such as a probe displacement sensor 290, a calibration chip 295 and/or a synchronization module 280.

In some embodiments, the cable may also include a tensile strain relief member, such as a steel cable (or other high tensile strength and low stretch material) configured to carry substantially an entire mechanical tensile load applied between the probe 200 and the connector 325.

In some embodiments, cable arrangements within a multiple aperture imaging probe may be uniquely configured for high quality transmission of electronic signals between each individual transducer element and an imaging control system (e.g., MAUI electronics or another host control system). In some embodiments, each transducer element may be electrically connected to an imaging control system with a unique differential pair of conductors. Such arrangements substantially reduce difficulties caused by cross-talk and other forms of electrical and/or electromagnetic interference.

In some embodiments, a probe may also be provided with a separate chassis ground circuit that is separate from any of the individual element grounds. In some embodiments, the chassis ground circuit may also be electrically connected to a shielding conductor surrounding other conductors in a cable bundle extending from the probe to a connector. An imaging control system may be configured to join the shield ground to a true earth ground. In some embodiments, an interior surface of a probe housing may also include a continuous electrically conductive layer for providing further shielding.

Figure 2C:
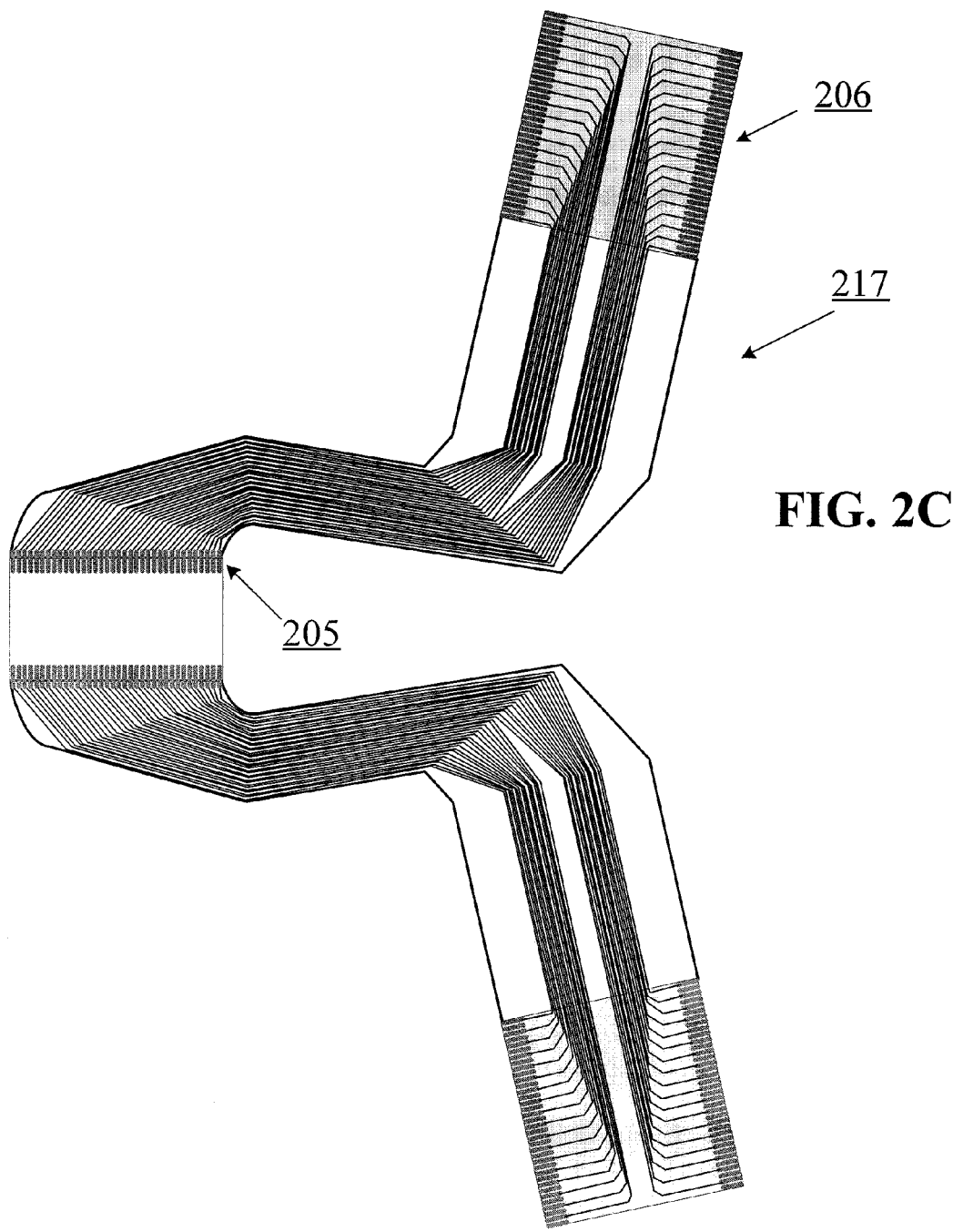
FIG. 2C is a diagram of one embodiment of a flex circuit for electrically connecting a single transducer array to probe electronic circuits.

FIGS. 2B and 2C illustrate an embodiment of a unique flex circuit 217 for electrically connecting a transducer array to a flex/PC board 218 which may be further connected to a cable. In some embodiments, a flex circuit 217 may provide a differential pair electrical connection from each element of a transducer array to a terminal end 219. FIG. 2B illustrates a circuit 217 with an element-connection end connected to a backing block of a transducer array. FIG. 2C illustrates a two-sided flex circuit 217 with two rows of element connectors 205 configured to be electrically connected to elements of a transducer array. The element connectors 221 of the flex circuit 217 may be electrically connected to the array's elements either in manufacturing or after via surface mount connectors, surface solder joints or any other suitable method. In alternative embodiments, individual cables may be used in place of flex circuits for electrically connecting transducer array elements to a PC board or directly to a cable.

Figure 2D:
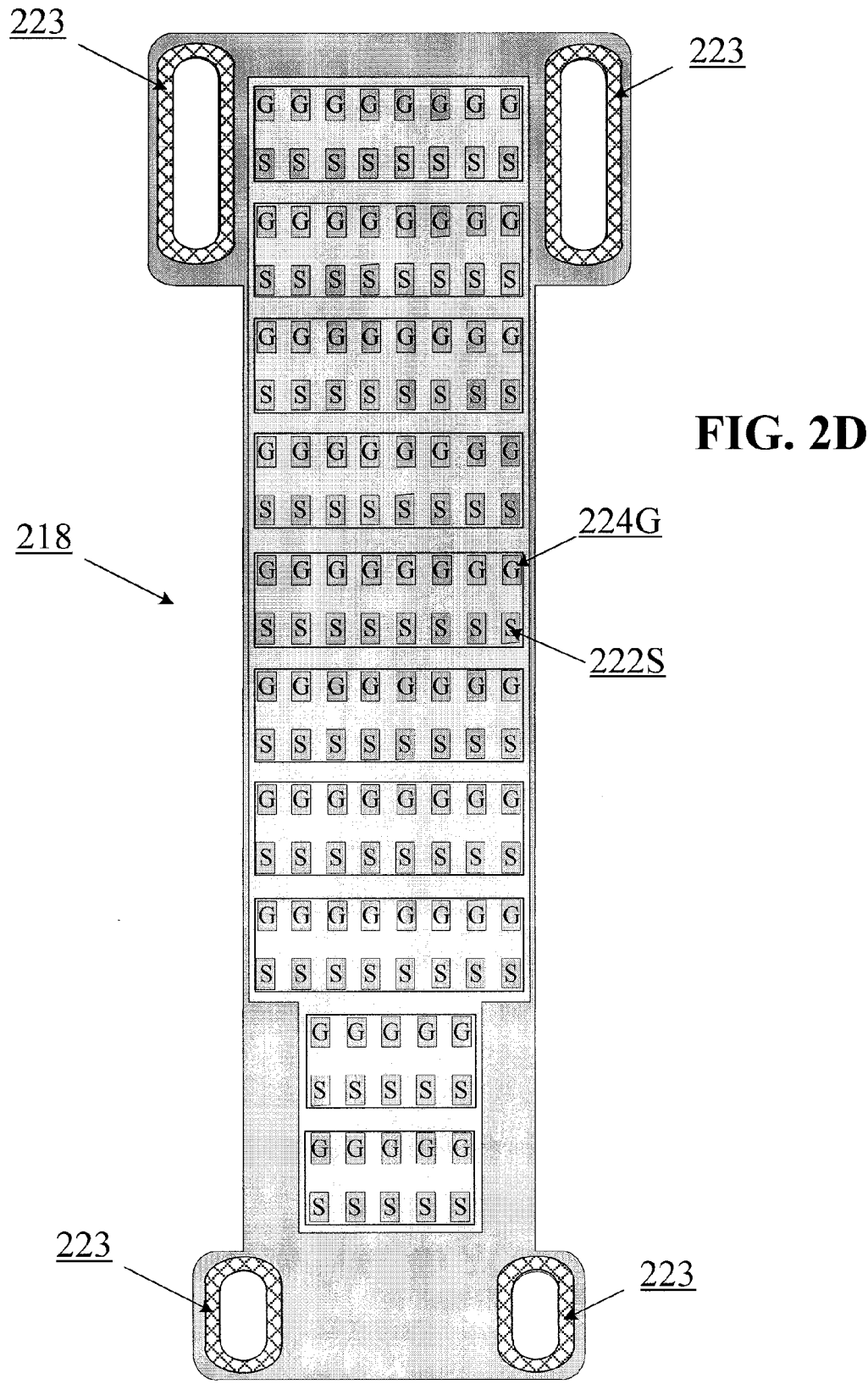
FIG. 2D is a diagram of one embodiment of a flex/PC board that may provide electrical connections between flex circuits and coaxial cables.
Figure 2E:
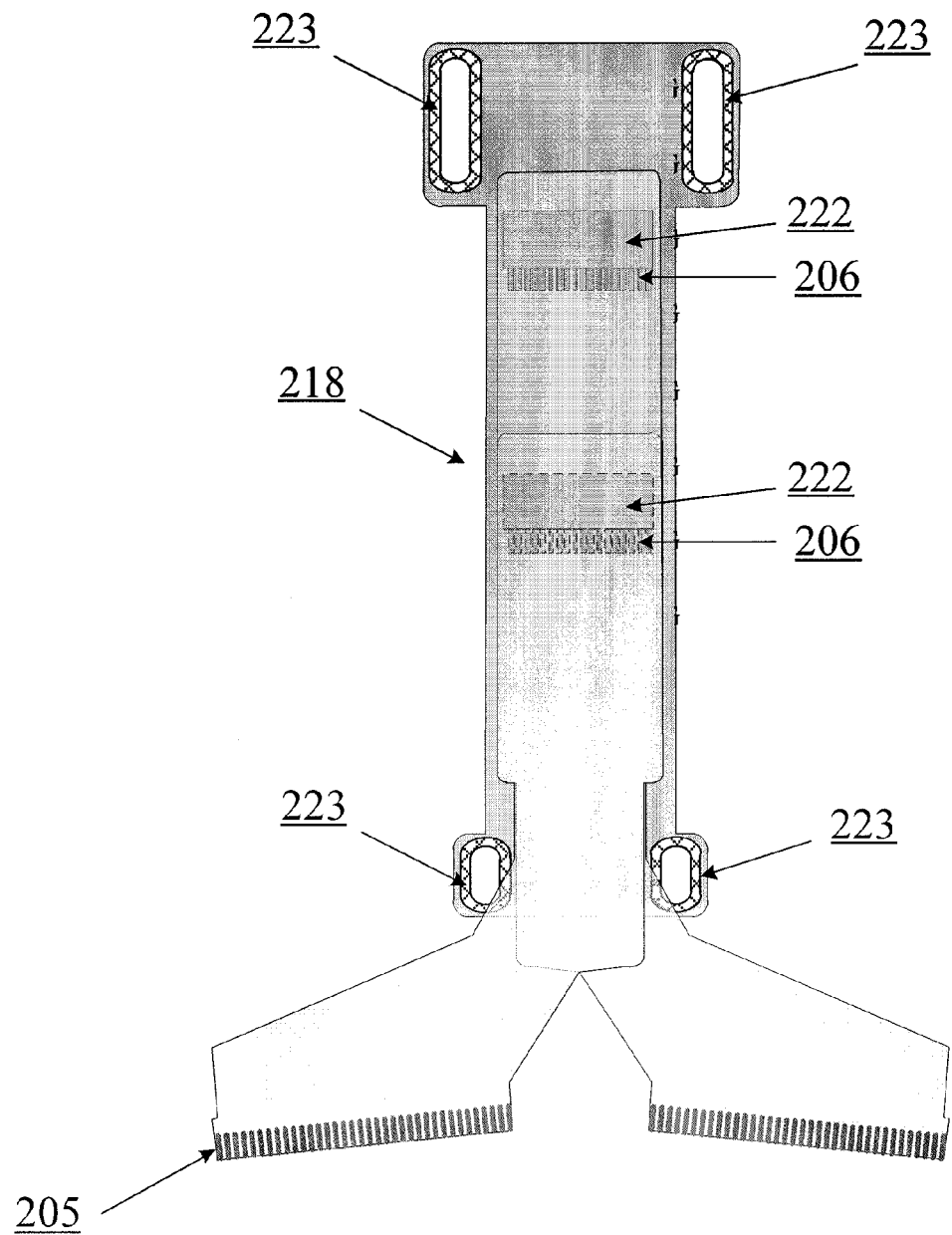
FIG. 2E is a diagram illustrating an embodiment of multiple custom flex circuits terminating onto a flex/PC board.

In some embodiments, the terminal end 219 of a flex circuit 217 may include an array of connectors 206 configured to be connected to corresponding flex terminal connectors 222 on a first side of the flex/PC board 218. FIG. 2E illustrates the flex connector side of the flex/PC board 218 with a pair of flex circuits 217 connected to a flex/PC board 218. In some embodiments, a flex/PC board 218 may be a substantially rigid printed circuit board with one or more flex terminal connectors 222 on one face, and an array of cable terminals on the opposite face. In some embodiments, circuit conductors may be printed into the board to provide electrical connections between flex circuit conductors and corresponding cable terminals. The flex/PC board 218 may also include grounding pads 223 which may be electrically connected to the chassis ground circuit.

In some embodiments, a flex/PC board 218 may be configured to keep the signal coaxial cables grounded separately from the chassis and/or outer cable shielding ground. FIG. 2D illustrates an array of connection terminals on the cable-connector side of the flex/PC board 218. As shown, the array of connections may include rows of ground terminals 224G paired with rows of signal terminals 224S.

Figure 2F:
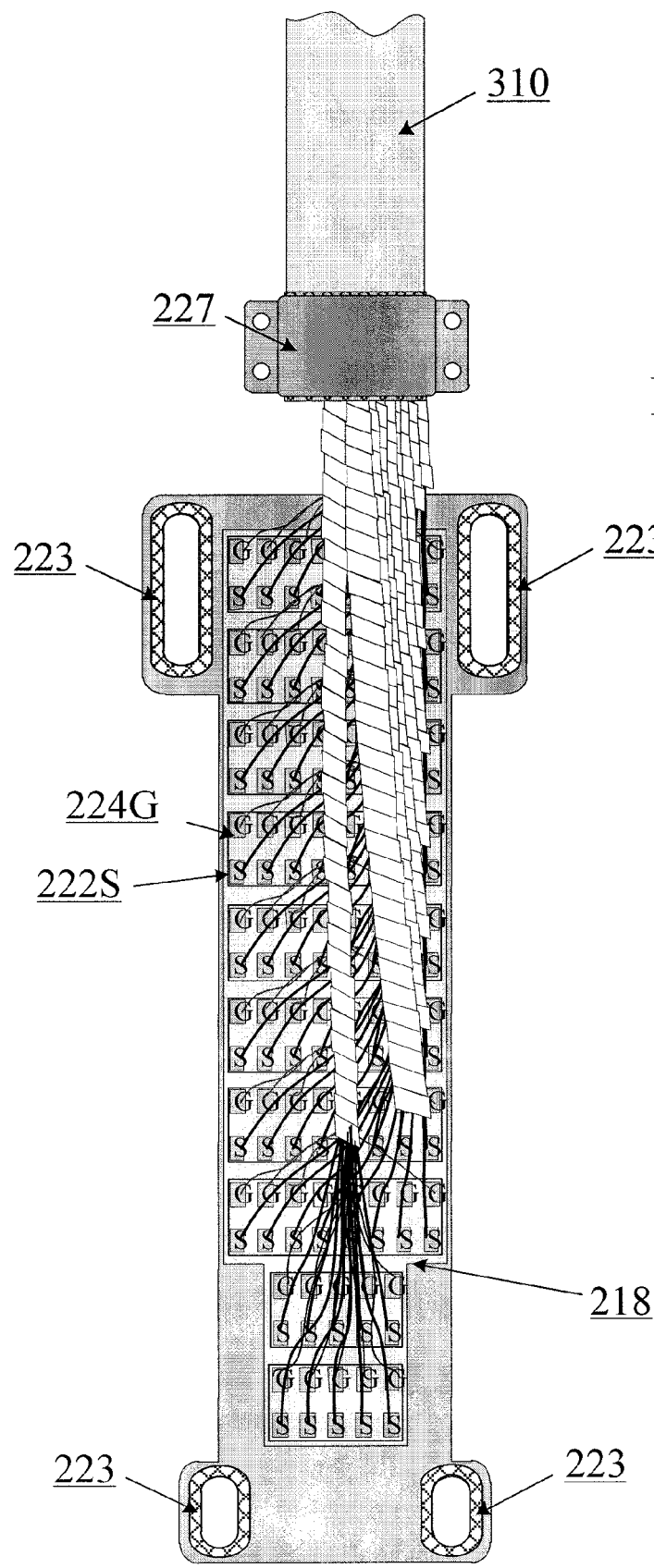
FIG. 2F is a diagram illustrating an embodiment of connections between bundles of coaxial cables and a flex/PC board.

FIG. 2F illustrates the connections of the individual coaxial cables from the cable bundle 310 to individual element-specific terminals on the flex/PC board 218. Each coaxial cable in the cable bundle may include an outer insulator, a shield conductor, an inner insulator and a central conductor. The central conductor may be referred to as the signal conductor, because it normally carries the electrical signals from the imaging control system to the transducer elements and back. In some embodiments, coaxial cables may be micro-coaxial cables (or "microcoax" cables), which may be about 42 gauge to about 58 gauge (or about 0.0025 inches to about 0.00039 inches in diameter).

In some embodiments, the signal conductor of each coaxial cable may be soldered to a corresponding signal terminal 224S, and the shield conductor of the same coaxial cable may be soldered to a corresponding ground terminal 224G. Thus, in some embodiments, there is no electrical path from a particular signal ground to any other signal ground. Similarly, embodiments may be configured such that no signal ground has an electrical path to the common chassis ground.

In some embodiments, coaxial cable conductors may be soldered directly to the contacts of the flex/PC board 218. In other embodiments, various mechanical connectors or clamps may alternatively be used. In further embodiments, any other wiring harness or connector may be used as desired.

As shown in FIG. 2F, a cable clamp 227 may also be provided to provide mechanical and/or electrical connection to the probe housing. In some embodiments, the cable clamp 227 may be electrically connected to the chassis ground tabs 223. In some embodiments, the cable clamp 227 may also be mechanically connected to the flex/PC board or directly to the probe housing. The cable clamp may also provide a mechanical attachment for a tensile strain relief element of the cable.

In some embodiments, a flex/PC board may also be configured to perform other functions by including additional integrated circuit chips soldered or otherwise electrically connected to the board.

In some embodiments, the flex/PC board may be used to re-task elements to either transmit or receive functions, such as by using dynamic electronic switching arrangements, or by configuring the connection of coaxial cables to terminals in varying arrangements.

In some embodiments, the flex/PC board may be used to arbitrate signals so that fewer cables are required in the bundles. For example, in some embodiments, a single coaxial cable may be electrically connected to the contacts of more than one transducer element (e.g., by using jumpers to connect selected terminals 224). In other embodiments, electronic switches may be provided on the flex/PC board to allow for dynamic switching of the relationship between a transducer element and a coaxial cable. Thus, in some embodiments, a cable bundle 310 may include fewer cable pairs than the number of individual transducer elements, while still providing substantial benefits of connecting elements with differential conductor pairs.

In other embodiments, the flex/PC board may include components configured to arbitrate signals for transmission to imaging control electronics via one or more fiber optic cables. For example, electrical to fiber optic conversion components and fiber optic coupling components may be mounted to the flex/PC board in order to convert electrical signals from the transducer elements into optical signals to be transmitted to an imaging control system via a fiber optic cable bundle in place of the coaxial cable bundle 310.

In alternative embodiments, all coaxial cables may be omitted, and a wireless communications chip may be provided in the probe housing and configured to communicate with an ultrasound imaging control system wirelessly. In some embodiments, such a wireless communications chip may be based on one or more common wireless data transmission standards, such as the IEEE 802.11 standards (e.g., "WiFi"), IEEE 802.15 standards (e.g., "Bluetooth") or others. A wireless communications chip may be soldered or otherwise connected to a flex/PC board which may also include flex connectors electrically connected to flex circuits connected to transducer arrays.

Figure 5:
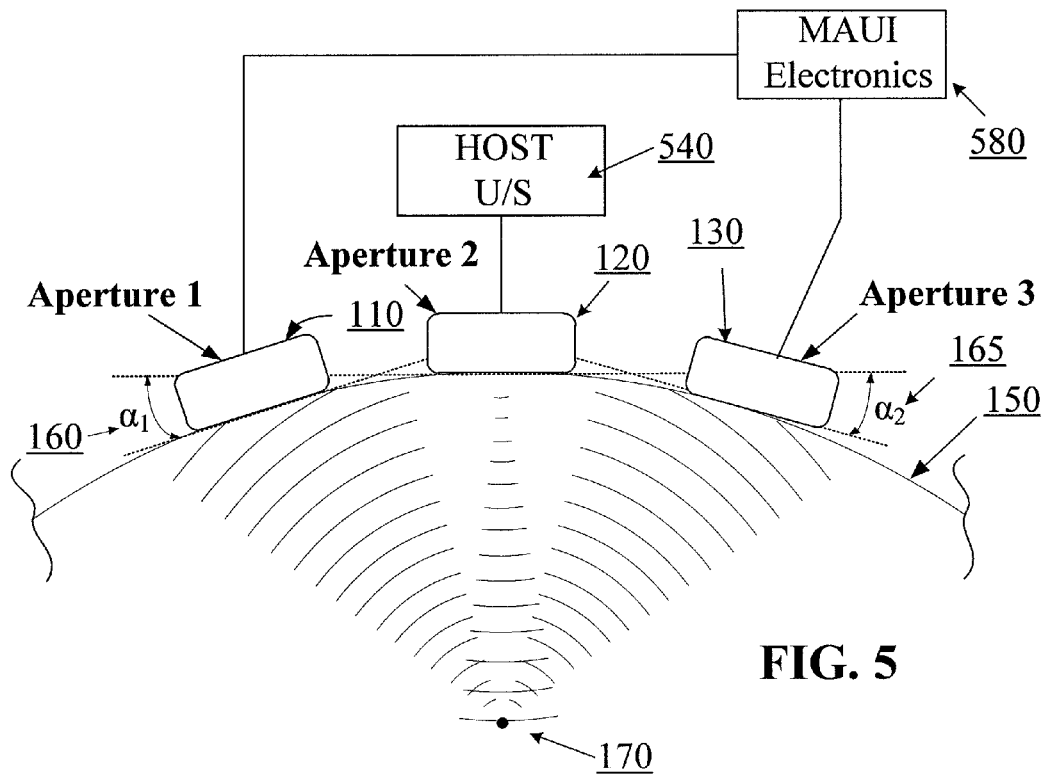
FIG. 5 is a block diagram illustrating an embodiment of transmit and receive functions for a Multiple Aperture Ultrasound probe connected to a host ultrasound system and a separate add-on control system.
Figure 5A:
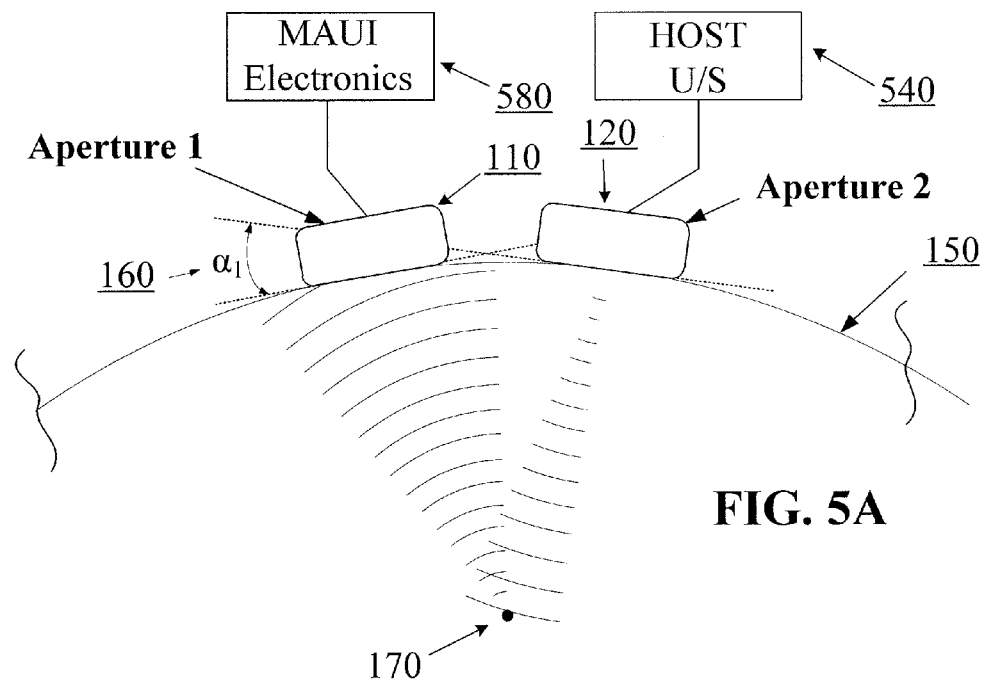
FIG. 5a is a block diagram illustrating an embodiment of transmit and receive functions for a Multiple Aperture Ultrasound probe used in a two array format.

Some embodiments of multiple aperture probes can also be constructed to operate as add-on devices to any ultrasound imaging host system, even those not specifically configured to operate multiple aperture probes. FIGS. 5 and 5A provide block diagrams illustrating two multiple aperture ultrasound imaging operations utilizing a standard host ultrasound system and a multiple aperture ultrasound imaging add-on device. In the example of FIG. 5, the center array 120 may be used for transmit only. The lateral arrays 110 and 130 may be used for receive only. The embodiment of FIG. 5A demonstrates the right array 120 being used to transmit, and the left array 110 being used to receive ultrasound signals.

Figure 6:
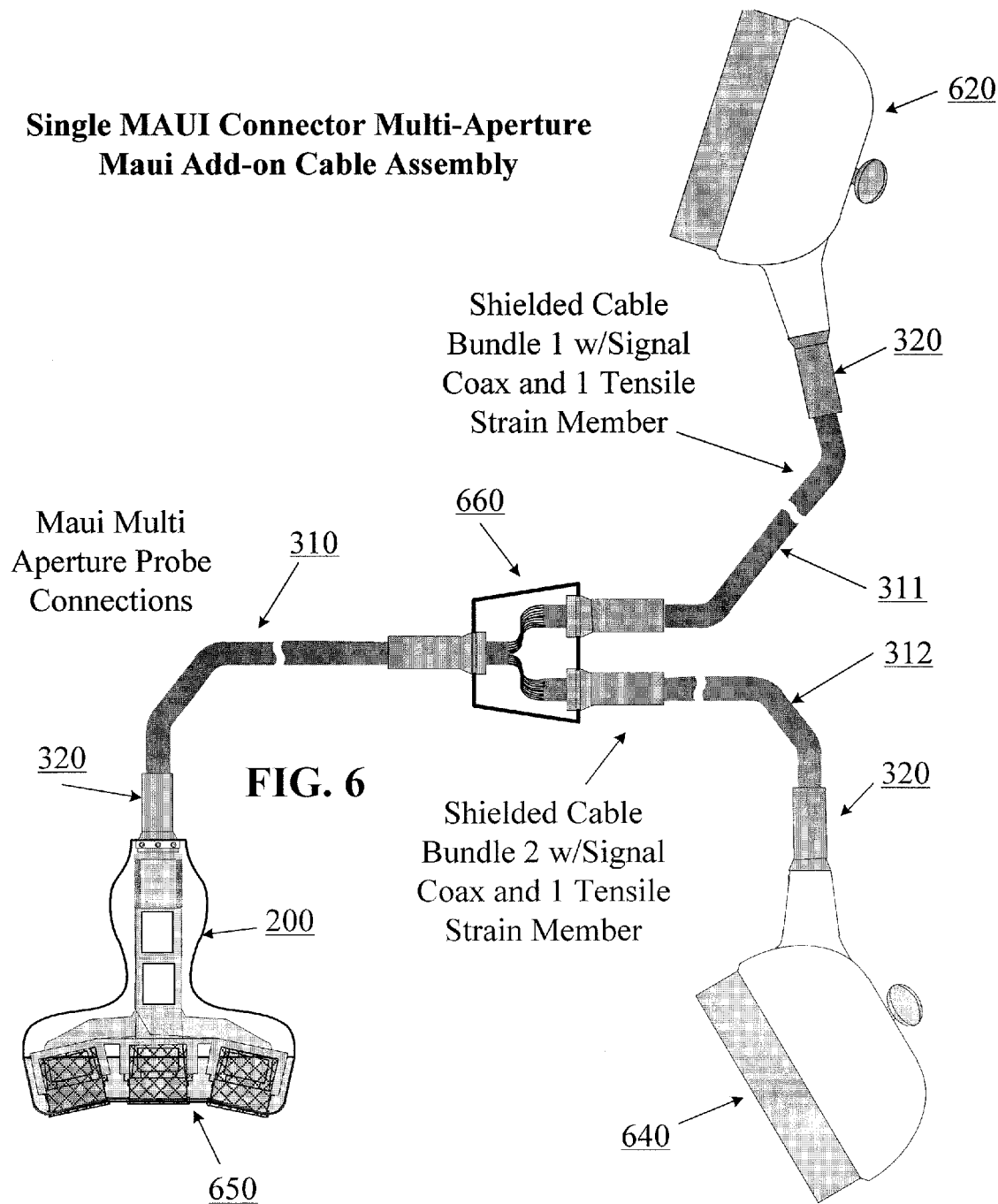
FIG. 6 illustrates an embodiment of a multiple aperture probe, cable and connector assembly configured for connection to both a host ultrasound imaging control system and an add-on imaging control system.

FIG. 6 illustrates an embodiment of a three-array multiple aperture probe 200 with cables and connectors for using the probe with an add-on system. Such a system may include substantially similar construction discussed above from the probe 200 to the junction box 660. From the junction box, the bundle of coaxial cables may be divided into a first cable branch 311 with a first connector 620 and a second branch 312 with a second connector 640. The first connector 620 may be configured to be attached to a host ultrasound system which provides transmit energy to the transmit array. The second connector 640 may be configured to connect to a stand-alone MAUI electronics system configured to receive and interpret echoes to generate images. Like the single system, the add-on system cabling coming from the multiple aperture probe may be bundled together so as to provide ease of use and maneuverability for an operator. In some embodiments, cable junction boxes 660 and strain reliefs 320 may be used on all cables.

FIGS. 7-13A provide several additional embodiments illustrating examples of multiple aperture ultrasound probe construction and cable assemblies. These examples represent some of the possible application-specific multiple aperture probes that may be constructed. Many variations in size and layout of each of the probes described herein are also possible.

Figure 7B:
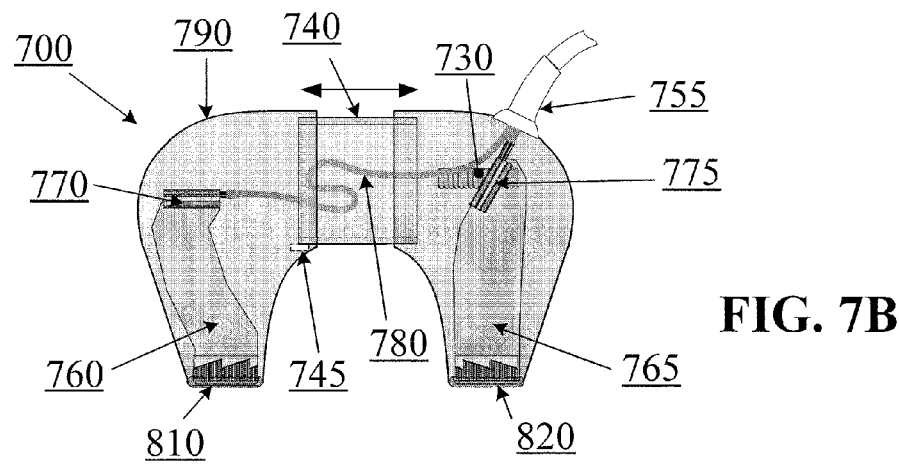
FIG. 7B shows the probe of FIG. 7A in an extended configuration with internal components visible.

FIGS. 7-7B illustrate an embodiment of a multiple aperture probe 700 having a design and features that make it particularly well suited for cardiac applications. As illustrated in FIG. 7, some embodiments of a multiple aperture probe 700 may include a pair of legs 710, 720 joined by a common central portion 740. In the embodiment of FIG. 7, the central body portion 740 is configured to allow the legs to slide relative to one another. Each leg portion 710, 720 may include a transducer array 810, 820 respectively on a lower surface.

In some embodiments, a sensor 775 can be provided on or adjacent to the slidable central portion 740. Such a sensor can be configured to transmit mechanical position information of each of the legs 710, 720 back to the MAUI electronics. Suitable sensors may include optical sensors, digital encoders, potentiometers or any other suitable sensor.

The embodiment in FIG. 7 illustrates a thumb wheel 730 that may be used to physically adjust the position of the legs 710, 720. In alternative embodiments, any other mechanism or device may be provided to control size adjustment of the probe.

In the illustrated embodiment, one leg of the probe 710 may encase one flex circuit 760, and the other leg 720 may encase a separate flex circuit 765. The flex circuits in these embodiments may be any of the types described above, Similarly to the embodiments above, the probe may include individual flex circuits 760, 765 in each leg 710, 720. The flex circuits may be attached via connectors to separate flex/pc boards 770, 775 configured with suitable shapes and sizes to fit within the probe housing. In some embodiments, the extender 740 section may enclose an extra length of coaxial cable bundles 780 as slack to accommodate adjustment of the legs. The cables may then be bundled together and inserted into strain relief 755.

Figure 8:
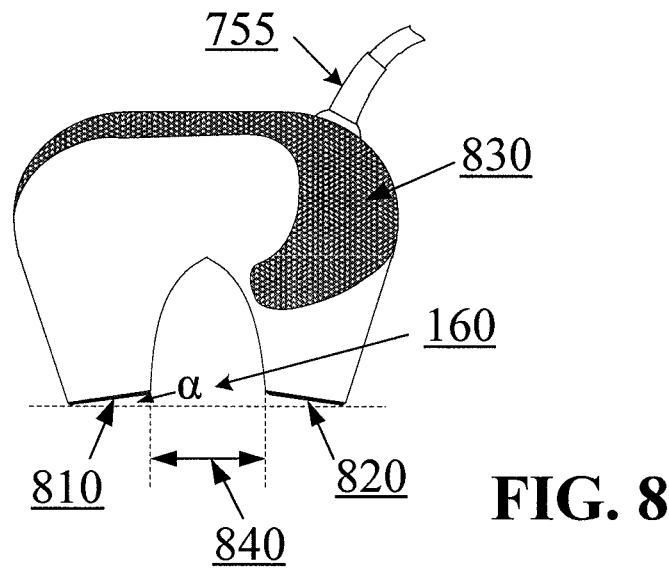
FIG. 8 illustrates an embodiment of a hand-held two-array multiple aperture probe with a non-adjustable fixed width.

FIG. 8 illustrates an embodiment of a fixed-position multiple aperture probe of similar shape to those shown in FIGS. 7-7B. The distance between the legs 840 may be fixed to be used in cardiac applications where it is desirable to "see" between or around ribs and through the intercostal spaces. Such probes may also be useful in other applications.

Figure 8A:
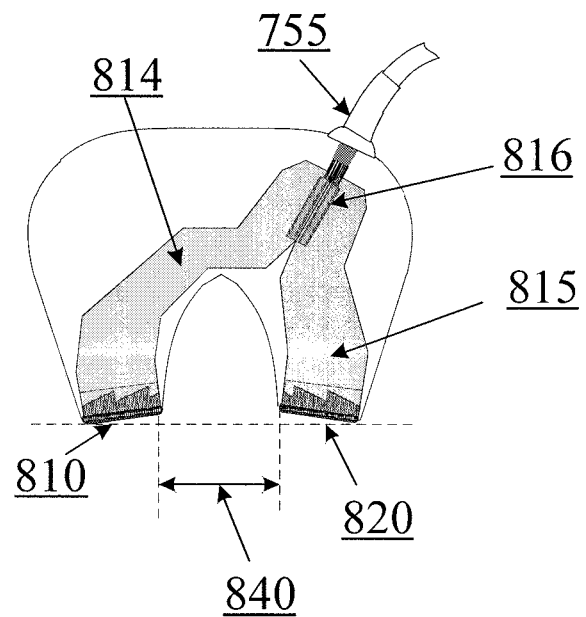
FIG. 8A illustrates an embodiment of the probe of FIG. 8 with internal components visible.

In the embodiment of FIG. 8A, the arrays are shown angled 160 for optimizing beamforming characteristics as discussed above. In some embodiments, the arrays of any of the probes of FIGS. 7-8A may be mounted to respective backing plates similar to those described above for the purpose of securely holding the arrays in a desired position. Such backing plates may be configured to secure and position the arrays at a desired angle, a.

The embodiments shown in FIGS. 9-9B provide a multiple aperture ultrasound Probe for very high resolution imaging by inserting the probe into a body lumen, such as a patient's esophagus. The embodiments of FIGS. 9-9B provide an ultrasound probe that may be mounted to a distal end of an elongate catheter or endoscope configured for positioning and steering the distal probe to a desired position within a body lumen.

FIG. 9 illustrates an embodiment of an Omniplane Style Transesophogeal probe where FIG. 9A is a cut away top view and FIG. 9B is a cut away side view. In this embodiment, an enclosure 940 may contain multiple aperture arrays 910, 920 and 930 that are contained and positioned on a backing plate 992. The backing plate may be mounted on a rotating turn table 982 which can be operated mechanically or electrically to rotate the arrays about an axis perpendicular to the surface of the center array (i.e., an axis perpendicular to the longitudinal axis of the catheter). The enclosure 940 may contain suitable echo-lucent material to facilitate the transfer of ultrasound echo information with a minimum of degradation, and is contained by an acoustic window 950. The operator may manipulate the probe with controls 990 located inside the flex circuit 991. In some embodiments, the flex circuit 991 may be coiled around the arrays allowing the operator to change the arrays' orientation with adequate slack.

In FIG. 9A, the flex circuit 991 is shown terminating into the ends of the elements of each array at 992.

In FIG. 9B, the arrays 910, 920, 930 are shown physically separated from each by a length 980 of a backing block 984. In some such embodiments, each array 910, 920, 930 may have a separate flex connection 992. In some embodiments, coaxial cables may be connected to the common terminal 990 and then placed into a common cable as described above.

Figure 10:
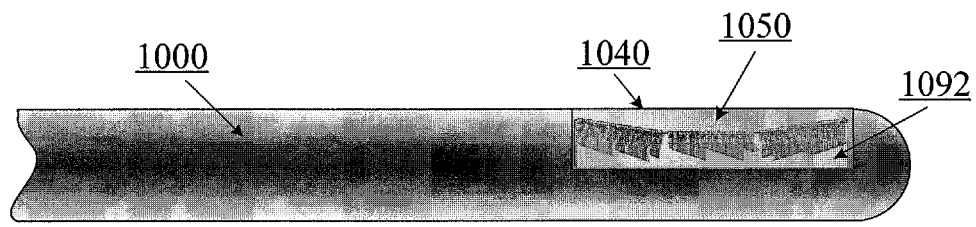
FIG. 10 illustrates an embodiment of a multiple aperture intracavity probe using three arrays with a center array recessed to a point in line with the trailing edges of the outboard arrays with the outboard arrays canted at an angle α. A unified lens may be provided for ease of use as part of the external probe encasement.
Figure 10A:
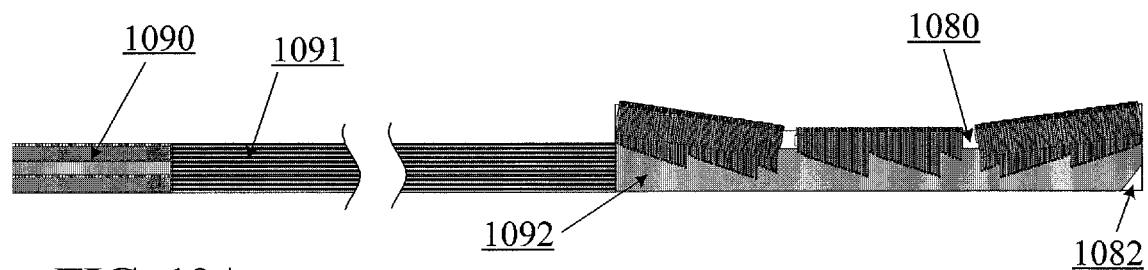
FIG. 10A illustrates a side view of the probe of FIG. 10, showing individual arrays secured and positioned by a backing plate.
Figure 10B:
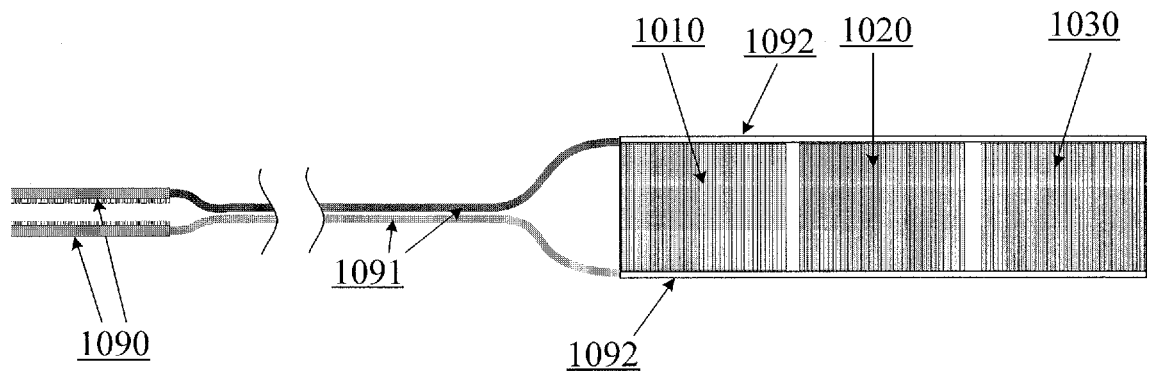
FIG. 10B is a top view of the probe of FIG. 10, showing three arrays and associated cabling internal to an intracavity probe without the encasement.

FIG. 10 illustrates an embodiment of an intracavity probe where FIG. 10A is a cut away side view and FIG. 10B is a cut away top view. In some embodiments, an enclosure 1000 may contain multiple aperture arrays 1010, 1020 and 1030 that are captured and positioned by a backing plate 1082. The enclosure 1000 may contain suitable echo-lucent material 1050 to facilitate the transfer of ultrasound echo information with a minimum of degradation, and may be contained by an acoustic window 1040.

As shown in FIG. 10A, the arrays may be physically separated from each other and held in the shown position by a backing plate 1082. In some embodiments, each array may have a separate flex circuit 1092. The flex circuit 1092 may extend the length of the enclosure 1000 until the flex circuit 1092 reaches the flex/PC board 1090. Coaxial cables extending from a connector may be connected to the flex/PC board 1090. The flex circuits and the coaxial cable may be connected via the flex/PC board in the enclosure.

As shown in FIG. 10B, the flex circuit 1091 may into the ends of each array's elements at 1092.

Figure 11:
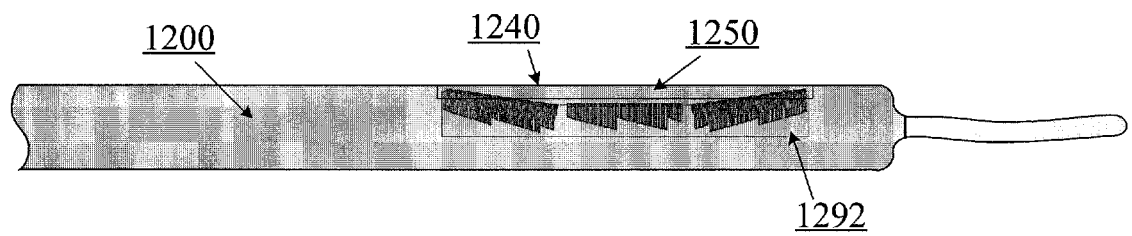
FIG. 11 is a side view of an embodiment of a multiple aperture intravenous ultrasound probe (IVUS) with three arrays where the center array is recessed from a point in line with the trailing edges of the outboard arrays with the outboard arrays canted at an angle α. A unified lens may be provided as part of the external probe encasement.
Figure 11A:
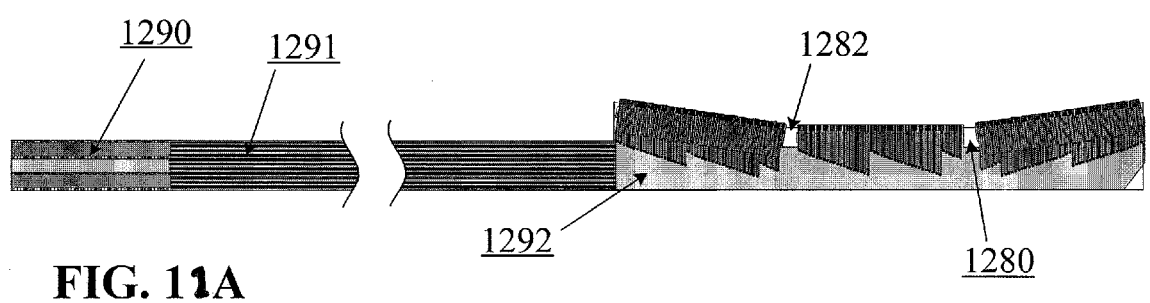
FIG. 11A illustrates a side view of the probe of FIG. 11 showing individual arrays secured and positioned by a backing plate.
Figure 11B:
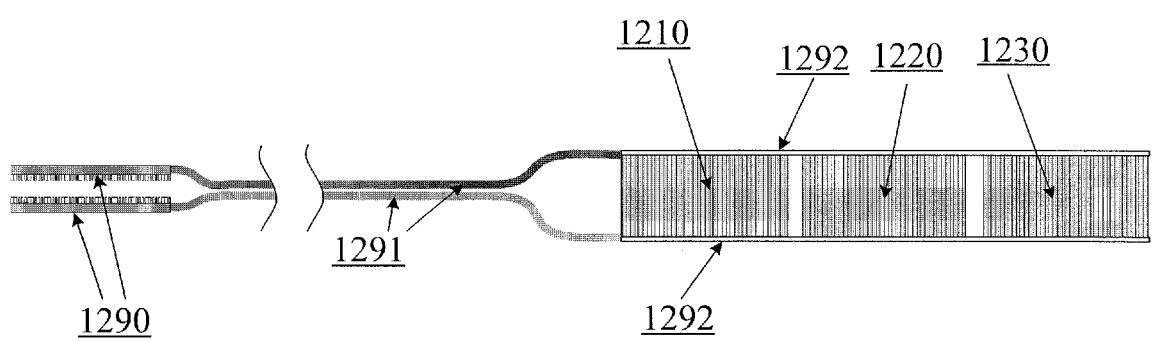
FIG. 11B is a top view of the probe of FIG. 11, showing associated cabling internal to the IVUS probe without the encasement.

FIG. 11 illustrates an embodiment of an Intravenous Ultrasound (IVUS) probe where FIG. 11A is a cut away side view and FIG. 11B is a cut-away top view. In this embodiment, an enclosure 1200 contains multiple aperture arrays 1210, 1220 and 1230 that are captured and positioned by a backing plate 1282. The enclosure 1200 may contain suitable echo-lucent material 1250 to facilitate the transfer of ultrasound echo information with a minimum of degradation, and may be contained by an acoustic window 1240.

As shown in FIG. 11A, the arrays may be physically separated from each other and held in the shown position by a backing plate 1282. In some embodiments, each array may have a separate flex circuit 1292. The flex circuit may extend the length of the enclosure until it reaches the flex/PC board 1290. Coaxial cables extending from a connector may be connected to the flex/PC board 1290. The flex circuits and the coaxial cable may be connected to one another via the flex/PC board in the enclosure.

In FIG. 11B, the flex circuit 1291 is shown terminating into the ends of each array's elements at 1292.

Figure 12:
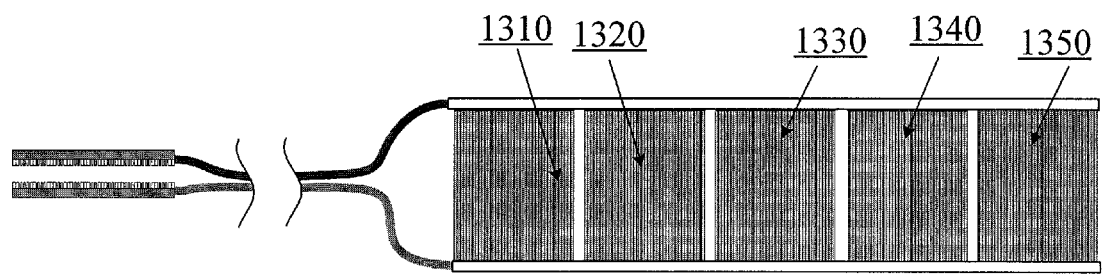
FIG. 12 illustrates a top view of an embodiment of a five array ultrasound probe.
Figure 12:
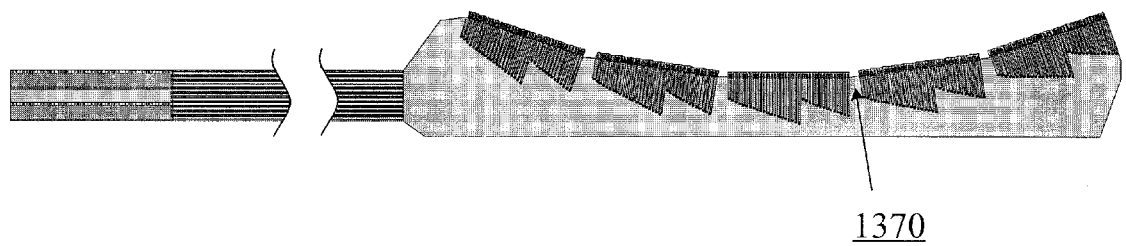

FIGS. 12-12A illustrates an embodiment of a multiple aperture probe configuration having five arrays 1310, 1320, 1330, 1340 and 1350 that could be used in many of the probes above. While there are five arrays demonstrated here, other embodiments may be configured to utilize more or fewer than five arrays. The number, size, spacing and orientation of the arrays in a particular embodiment may vary depending upon the target application of the probe. Arrays can be as small as an individual element (similar to a pedoff probe) and as large as a matrixed array that covers an entire body cavity. Consequently, arrays need not be positioned within the same transducer housing, furthering the benefits from accurate cable assemblies.

There also is no specific distance 1370 that must separate elements or arrays. The constraints of a symmetrical probe design are diminished by the greater flexibility in array placement enabled by embodiments of the present invention.

Terms such as "optimized," "optimum," "precise," "exact" and similar terms used in relation to quantitative parameters are merely intended to indicate design parameters which may be controlled or varied in accordance with general engineering principles. Use of these terms is not intended to imply or require that the parameters or components thereof are designed for the best possible or theoretical performance.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

What is claimed is:

1. A multiple aperture ultrasound probe, comprising:
 a probe housing containing a first ultrasound array of transducer elements and a second ultrasound array of transducer elements;
 a flex/PC board comprising a plurality of signal and ground terminals corresponding to the transducer elements of the first and second ultrasound arrays;
 a first flex circuit comprising a plurality of differential pairs of signal and ground conductors, the first flex circuit being configured to connect each transducer element of the first ultrasound array to its corresponding signal and ground terminals on the flex/PC board with one of the differential pairs of signal and ground conductors of the first flex circuit;
 a second flex circuit comprising a plurality of differential pairs of signal and ground conductors, the second flex circuit being configured to connect each transducer element of the second ultrasound array to its corresponding signal and ground terminals of the flex/PC board with one of the differential pairs of signal and ground conductors of the second flex circuit;
 first and second groups of coaxial cables comprising a plurality of differential coaxial signal and ground conductors, the groups of coaxial cables being configured to connect the signal and ground terminals of the flex/PC board corresponding to the transducer elements of the first and second ultrasound arrays to an imaging controller with the differential coaxial signal and ground conductors of the first and second groups of coaxial cables; and
 a backing plate configured to secure the first and second ultrasound arrays in predetermined positions and orientations relative to one another, the backing plate comprising a chassis ground circuit separate from the ground conductors of the first and second flex circuits and from the differential coaxial ground conductors of the coaxial cables.

2. The multiple aperture ultrasound probe of claim 1 wherein the backing plate internally supports the probe structure.

3. The multiple aperture ultrasound probe of claim 1 further comprising a calibration chip mounted on the flex/PC board.

4. The multiple aperture ultrasound probe of claim 3 wherein the calibration chip is configured to store position and orientation information about the first and second ultrasound arrays.

5. The multiple aperture ultrasound probe of claim 1 further comprising a probe position sensor mounted on the flex/PC board.

6. The multiple aperture ultrasound probe of claim 1 further comprising a synchronization module mounted on the flex/pc board, the synchronization module being configured to synchronize an add-on ultrasound device with the first and second ultrasound arrays.

7. The multiple aperture ultrasound probe of claim 1 further comprising:
a third ultrasound array of transducer elements secured to the backing plate;
a third flex circuit comprising a plurality of differential pairs of signal and ground conductors, the third flex circuit being configured to connect each transducer element of the third ultrasound array to its corresponding signal and ground terminals of the flex/PC board with one of the differential pairs of signal and ground conductors; and
a third group of coaxial cables comprising a plurality of differential coaxial signal and ground conductors, the third group of coaxial cables being configured to connect the signal and ground terminals of the flex/PC board corresponding to the transducer elements of the third ultrasound array to the imaging controller with the differential coaxial signal and ground conductors of the third group of coaxial cables.

8. The multiple aperture ultrasound probe of claim 1 wherein at least one of the first ultrasound array and the second ultrasound array comprises an internal flex cabling configured to accommodate movement of the first ultrasound array away from the second ultrasound array.

9. The multiple aperture ultrasound probe of claim 8 further comprising a sliding portion configured to allow the first ultrasound array and the second ultrasound array to move laterally relative to the probe housing.

10. The multiple aperture ultrasound probe of claim 1 wherein at least one of the first ultrasound array and the second ultrasound array is configured to rotate about an axis of the probe housing.

11. The multiple aperture ultrasound probe of claim 8, the probe housing further comprising a lever configured to move the first ultrasound array or the second ultrasound array relative to the probe housing.

12. The multiple aperture ultrasound probe of claim 8, the probe housing further comprising a dial and an electric motor configured to move the first ultrasound array or the second ultrasound array relative to the probe housing.

13. The multiple aperture ultrasound probe of claim 1, wherein at least one of the signal and ground conductors of the first coaxial cable group is electrically connected to more than one transducer element of the first ultrasound array.

14. The multiple aperture ultrasound probe of claim 13 further comprising an electronic switch on the flex/PC board configured to allow for dynamic switching between the more than one transducer element of the first ultrasound array.

* * * * *